United States Patent
Akatsu et al.

(10) Patent No.: US 10,617,326 B2
(45) Date of Patent: Apr. 14, 2020

(54) RESPIRATION WAVEFORM DRAWING SYSTEM

(71) Applicant: Minebea Mitsumi Inc., Nagano (JP)

(72) Inventors: Hiroyuki Akatsu, Minato-ku (JP); Norihito Iida, Sagamihara (JP)

(73) Assignee: MINEBEA MITSUMI INC., Nagano (JP)

(*) Notice: Subject to any disclaimer, the term of this patent is extended or adjusted under 35 U.S.C. 154(b) by 0 days.

(21) Appl. No.: 16/191,808

(22) Filed: Nov. 15, 2018

(65) Prior Publication Data

US 2019/0183382 A1    Jun. 20, 2019

Related U.S. Application Data

(63) Continuation of application No. PCT/JP2017/018332, filed on May 16, 2017.

(30) Foreign Application Priority Data

May 17, 2016   (JP) ................................ 2016-098864

(51) Int. Cl.
  *A61B 5/08*     (2006.01)
  *A61G 7/05*     (2006.01)
  (Continued)

(52) U.S. Cl.
  CPC .............. *A61B 5/0803* (2013.01); *A61B 5/08* (2013.01); *A61B 5/113* (2013.01); *A61G 7/05* (2013.01);
  (Continued)

(58) Field of Classification Search
  CPC ...... A61G 7/0527; A61G 7/05; A61B 5/0803; A61B 5/0816; A61B 5/113; A61B 5/00; A61B 5/08
  See application file for complete search history.

(56) References Cited

U.S. PATENT DOCUMENTS

| | | | |
|---|---|---|---|
| 9,339,215 B2 | 5/2016 | Van Vugt et al. | |
| 2005/0096559 A1* | 5/2005 | Yanai | A61B 5/113 600/534 |

(Continued)

FOREIGN PATENT DOCUMENTS

| | | |
|---|---|---|
| CN | 102078184 A | 6/2011 |
| CN | 103561648 A | 2/2014 |

(Continued)

OTHER PUBLICATIONS

International Search Report for International Application No. PCT/JP2017/018332 dated Aug. 1, 2017.

(Continued)

*Primary Examiner* — Christian Jang
(74) *Attorney, Agent, or Firm* — Pearne & Gordon LLP

(57) ABSTRACT

There is provided a respiratory waveform drawing system. The system includes load detectors; a center of gravity position calculation unit; an oscillation coordinate setting unit configured to perform: obtaining a first extreme point at which a distance between an initial origin and the position of the center of gravity of the subject is maximized; obtaining a second extreme point which appears at an opposite side of the initial origin from the first extreme point, and at which a distance between the initial origin and the position of the center of gravity of the subject is maximized; setting a direction connecting the first and second extreme points as a direction of a tentative oscillation axis; and setting a midpoint between the first and second extreme points as a tentative oscillation origin; and a waveform drawing unit configured to draw the respiratory waveform.

9 Claims, 16 Drawing Sheets

(51) Int. Cl.
   *A61B 5/113*   (2006.01)
   *A61B 5/00*   (2006.01)
(52) U.S. Cl.
   CPC ..... *A61B 5/6891* (2013.01); *A61B 2562/0252* (2013.01)

(56) References Cited

U.S. PATENT DOCUMENTS

2007/0191742 A1   8/2007   Park
2015/0073283 A1   3/2015   Van Vugt et al.

FOREIGN PATENT DOCUMENTS

| | | |
|---|---|---|
| DE | 10 2011 011 988 A1 | 8/2012 |
| JP | 53-092577 A | 8/1978 |
| JP | 61-24010 B2 | 6/1986 |
| JP | 3353460 B2 | 9/2002 |
| JP | 3353460 B2 | 12/2002 |
| JP | 2003-000552 A | 1/2003 |
| JP | 2006-149957 A | 6/2006 |
| JP | 4002905 B2 | 11/2007 |
| JP | 4829020 B2 | 11/2011 |
| JP | 4883380 B2 | 2/2012 |
| JP | 2014-180432 A | 9/2014 |
| WO | 03/000126 A1 | 1/2003 |
| WO | 2011/009085 A2 | 1/2011 |
| WO | 2013/179189 A1 | 5/2013 |
| WO | 2013/179189 A1 | 12/2013 |

OTHER PUBLICATIONS

Written Opinion for International Application No. PCT/JP2017/018332 dated Aug. 1, 2017 and English translation.
Chinese Office Action dated May 10, 2019 for corresponding Chinese Application No. 201780042223.6 and English translation.
Extended European Search Report dated Jan. 8, 2020 for corresponding European Application No. 17799367.2.

* cited by examiner

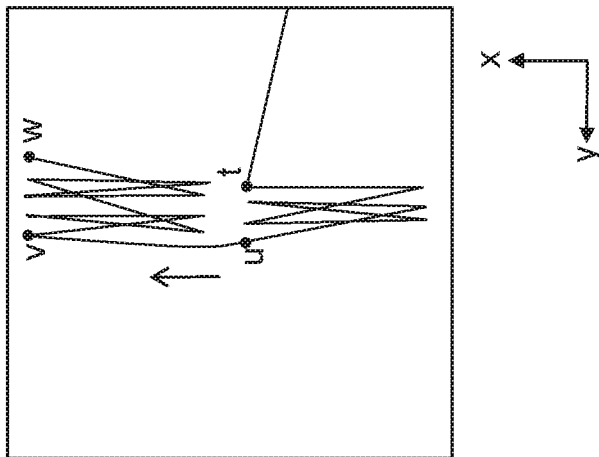
Fig. 9A  Fig. 9B  Fig. 9C
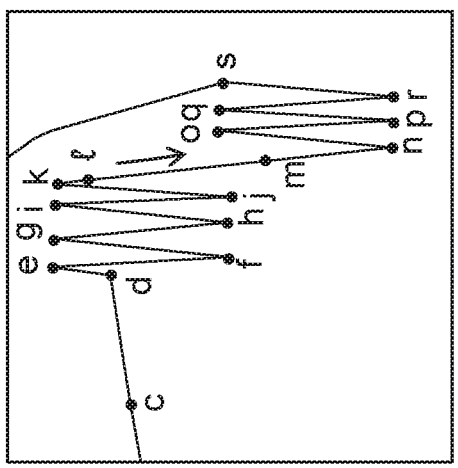
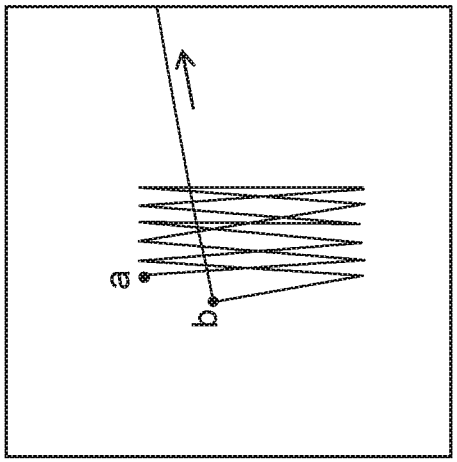

RESPIRATION WAVEFORM DRAWING SYSTEM

CROSS-REFERENCE TO RELATED APPLICATIONS

This application is a Continuation Application of International Application No. PCT/JP2017/018332 claiming the conventional priority of Japanese patent Application No. 2016-098864 filed on May 17, 2016, and titled "RESPIRATION WAVEFORM DRAWING SYSTEM". The disclosures of Japanese patent Application No. 2016-098864, and International Application No. PCT/JP2017/018332 are incorporated herein by reference in their entirety.

BACKGROUND

The present disclosure relates to a respiratory waveform (respiration waveform) drawing (graphing) system configured to draw (graph) a respiratory waveform of a subject on the basis of variation in the position of center of gravity of the subject.

Biological information of a subject (human subject, that is, a person being monitored) is one of important pieces of information for knowing the physical condition (body condition) of a patient or a care receiver in the sites of the medical treatment and the care. For example, respiratory condition of the subject can be grasped and utilized to grasp and improve (alleviate) the symptoms of, for example, the sleep apnea syndrome (SAS) and the snore.

It has been suggested that load sensors are arranged under legs of a bed to measure the respiratory condition of a subject on the basis of measured values of the load sensors (Japanese Patent No. 4883380). Further, it has been also suggested that load detectors are arranged under legs of a bed to obtain (acquire) the movement of the center of gravity of a subject living body on the bed so that the respiratory movement (breathing movement) and the heartbeat movement of the subject living body are obtained on the basis of the movement of the center of gravity (Japanese Publication of Examined Patent Application No. 61-24010).

SUMMARY

In sites of medical treatment, while it is desired to present a real-time waveform indicating a respiratory condition of a subject, the inventions according to Japanese Patent No. 4883380 and Japanese Publication of Examined Patent Application No. 61-24010 cannot satisfy such desire from the practice site.

In view of the above, an object of the present disclosure is to provide a respiratory waveform drawing system capable of presenting an almost real-time waveform indicating the respiration of a subject.

According to a first aspect of the present disclosure, there is provided a respiratory waveform drawing system for drawing a respiratory waveform of a subject on a bed, the system including: a plurality of load detectors which are to be placed in the bed or under legs of the bed, and which are configured to detect a load of the subject; a center of gravity position calculation unit configured to obtain a position of a center of gravity of the subject based on the load of the subject; an oscillation coordinate setting unit configured to perform: obtaining a first extreme point at which a distance between an initial origin and the position of the center of gravity of the subject shifting from the initial origin is maximized, the position of the center of gravity of the subject at a certain time point being used as the initial origin; obtaining a second extreme point which appears at an opposite side of the initial origin from the first extreme point, and at which a distance between the initial origin and the position of the center of gravity of the subject shifting from the first extreme point is maximized; setting a direction connecting the first and second extreme points as a direction of a tentative oscillation axis; and setting a midpoint between the first and second extreme points as a tentative oscillation origin; and a waveform drawing unit configured to draw the respiratory waveform by presenting a displacement, from the tentative oscillation origin, of a position obtained by projecting the position of the center of gravity of the subject onto the tentative oscillation axis, with respect to time.

BRIEF DESCRIPTION OF THE DRAWINGS

FIG. 9A is an enlarged view of the center of gravity locus depicted in area A of FIG. 8.

FIG. 9B is an enlarged view of the center of gravity locus depicted in area B of FIG. 8.

FIG. 9C is an enlarged view of the center of gravity locus depicted in area C of FIG. 8.

EMBODIMENTS

First Embodiment

A first embodiment of the present disclosure will be explained with reference to FIGS. 1 to 24.

Figure 1:
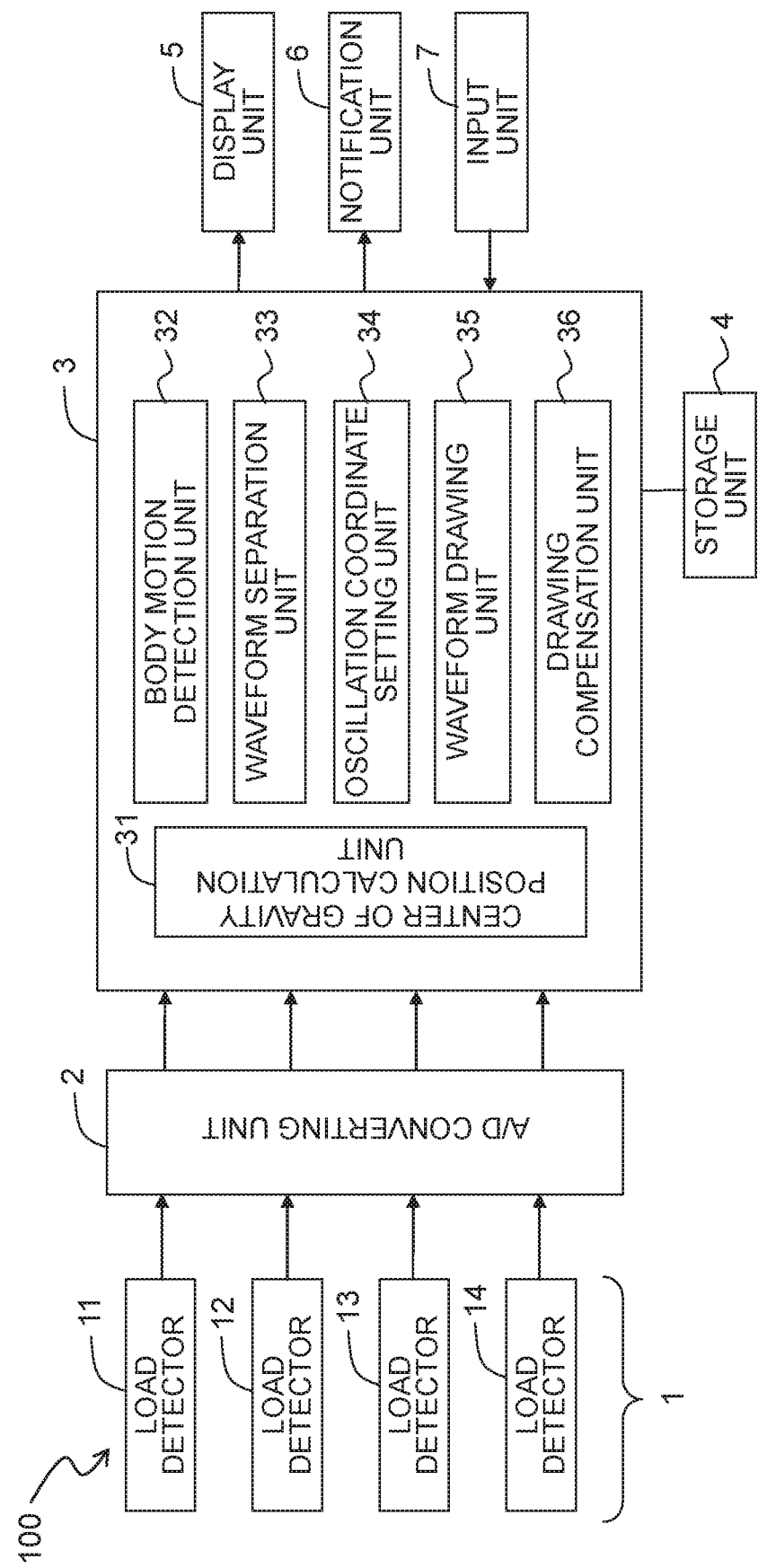
FIG. 1 is a block diagram depicting a configuration of a biological information monitoring system according to an embodiment of the present disclosure.

As depicted in FIG. 1, a biological information monitoring system (a respiratory waveform drawing system, a respiration information obtaining (acquisition) system) 100 of this embodiment is provided to perform the observation and/or the measurement in order to grasp the biological state or condition of a subject (a human subject, that is, a person being monitored) on a bed. The biological information monitoring system 100 principally includes a load detecting unit 1, a control unit (controller) 3, a storage unit (storage) 4, and a display unit 5. The load detecting unit 1 and the control unit 3 are connected via an A/D converting unit 2. A notification unit 6 and an input unit 7 are further connected to the control unit 3.

The load detecting unit 1 is provided with four load detectors 11, 12, 13, 14. Each of the load detectors 11, 12, 13, 14 is a load detector which detects the load by using, for example, a beam-type load cell. Such a load detector is described in, for example, Japanese Patent No. 4829020 and Japanese Patent No. 4002905. Each of the load detectors 11, 12, 13, 14 is connected to the A/D converting unit 2 by means of wiring.

Figure 3:
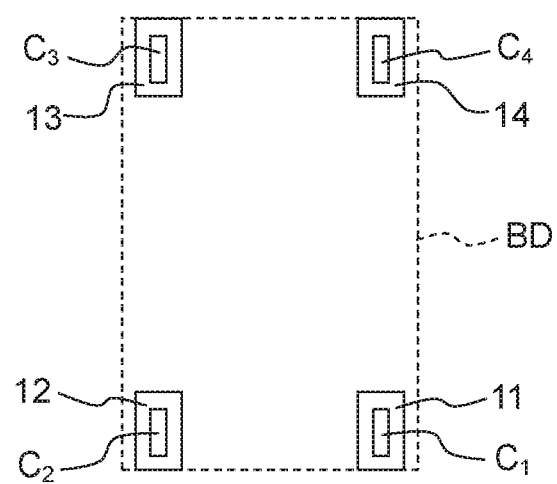
FIG. 3 is an illustrative view depicting an arrangement of load detectors with respect to a bed.

The four load detectors 11, 12, 13, 14 of the load detecting unit 1 are arranged under legs of a bed to be used by the subject. Specifically, as depicted in FIG. 3, the load detectors 11, 12, 13, 14 are arranged respectively on the undersides of casters $C_1$, $C_2$, $C_3$, $C_4$ attached to lower end portions of the legs disposed at the four corners of the bed BD.

The A/D converting unit 2 is provided with an A/D converter which converts an analog signal fed from the load detecting unit 1 into a digital signal. The A/D converting unit 2 is connected to each of the load detecting unit 1 and the control unit 3 by means of wiring.

The control unit 3 is an exclusive or general-purpose computer. A center of gravity position calculation unit (center of gravity position calculator) 31, a body motion detection unit (body motion detector) (body motion determining unit, body motion determiner) 32, a waveform separation unit (waveform separator) (load separation unit, load separator) 33, an oscillation coordinate setting unit 34, a waveform drawing unit 35, and a drawing compensation unit (drawing compensator) 36 are constructed therein.

The storage unit 4 is a storage device which stores the data used for the biological information monitoring system 100. For example, it is possible to use a hard disk (magnetic disk) therefore. The display unit 5 is a monitor, such as a liquid crystal monitor, for displaying the information outputted from the control unit 3 for a user of the biological information monitoring system 100.

The notification unit 6 is provided with a device for visually or auditorily performing predetermined notification on the basis of the information fed from the control unit 3, for example, a speaker. The input unit 7 is an interface for performing predetermined input for the control unit 3, and may be a keyboard and a mouse.

It is possible to detect and monitor various biological information, such as the respiratory condition of the subject on the bed, by using the biological information monitoring system 100 described above. The acquisition and the monitoring of various biological information are performed on the basis of the variation of the center of gravity position of the subject on the bed.

Figure 2:
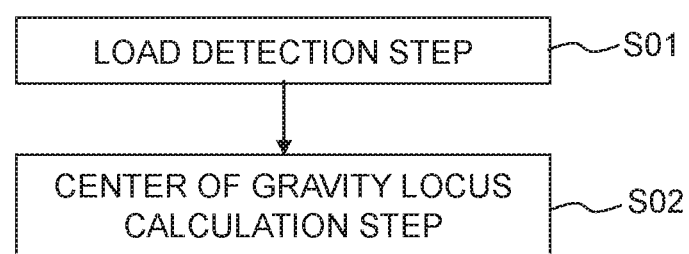
FIG. 2 is a flow chart depicting a method for calculating a locus of the center of gravity according to the embodiment of the present disclosure.

An explanation will be given about the operation for calculating the center of gravity position of the subject on the bed, by using the biological information monitoring system 100. As depicted in FIG. 2, the calculation of the center of gravity position of the subject, which is based on the use of the biological information monitoring system 100, includes a load detection step (S01) of detecting the load of the subject and a center of gravity locus calculation step (S02) of calculating the temporal variation of the position of the center of gravity of the subject (center of gravity locus) on the basis of the detected load.

Figure 4:
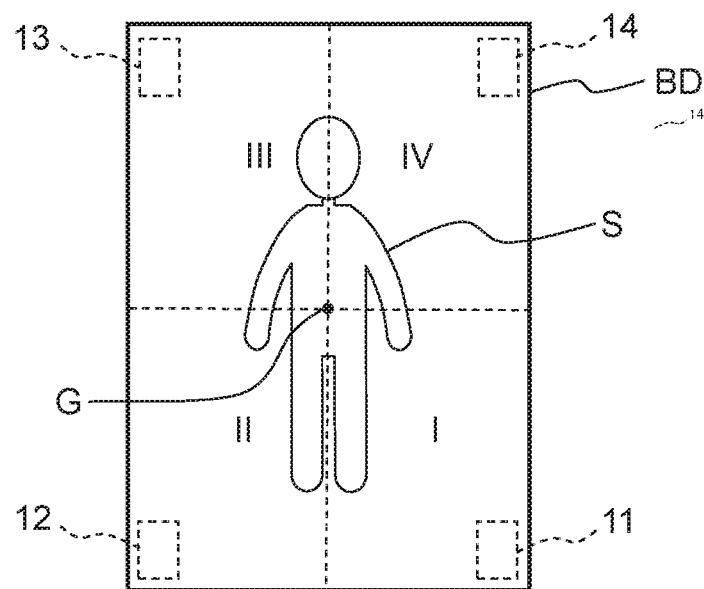
FIG. 4 is an illustrative view depicting an arrangement of four load detection areas defined on the upper surface of the bed.

In the load detection step S01, the load of the subject S on the bed BD is detected, by using the load detectors 11, 12, 13, 14. As the load detectors 11, 12, 13, 14 are arranged respectively on the undersides of the casters $C_1$, $C_2$, $C_3$, $C_4$ as described above, the load, which is applied to the upper surface of the bed BD, is detected in a dispersed manner by the four load detectors 11, 12, 13, 14. Specifically, as depicted in FIG. 4, the rectangular upper surface of the bed BD is longitudinally divided into two and laterally divided into two, and thus the upper surface is equally divided into four rectangular areas I to IV.

Accordingly, the load, which is applied to the area I positioned with the left lower half of the body of the subject S lying on his/her back (face up) at the central portion of the bed BD, is principally detected by the load detector 11, and the load, which is applied to the area II positioned with the right lower half of the body of the subject S in the same state, is principally detected by the load detector 12. Similarly, the load, which is applied to the area III positioned with the right upper half of the body of the subject S lying on his/her back at the central portion of the bed BD, is principally detected by the load detector 13, and the load, which is applied to the area IV positioned with the left upper half of the body of the subject S in the same state, is principally detected by the load detector 14. Note that when the subject S does not exist on the bed BD, the total of the outputs from the load detectors 11, 12, 13, 14 represents the weight of the bed itself. When the subject S exists on the bed BD, the total of the outputs from the load detectors 11, 12, 13, 14 represents the weight of the bed and the body weight of the subject S. Therefore, it is possible to measure the body weight of the subject S when the subject S exists on the bed, by previously storing the weight of the bed itself in the storage unit 4. Note that when the weight of the bed is not uniform among the four areas, the difference therebetween is stored beforehand as the bed weight corresponding to each of the load detectors. Further, it is desirable that the situation in which any weight other than that of the subject S is brought about during the actual measurement, for example, the placement of any bedding, any baggage or the like is reflected to the weight of the bed.

Each of the load detectors 11, 12, 13, 14 detects the load (load change), and the load (load change) is outputted as the analog signal to the A/D converting unit 2. The A/D converting unit 2 converts the analog signal into the digital signal while using the sampling period of, for example, 5 milliseconds, so as to output the digital signal (hereinafter referred to as "load signal") to the control unit 3.

Figure 5:
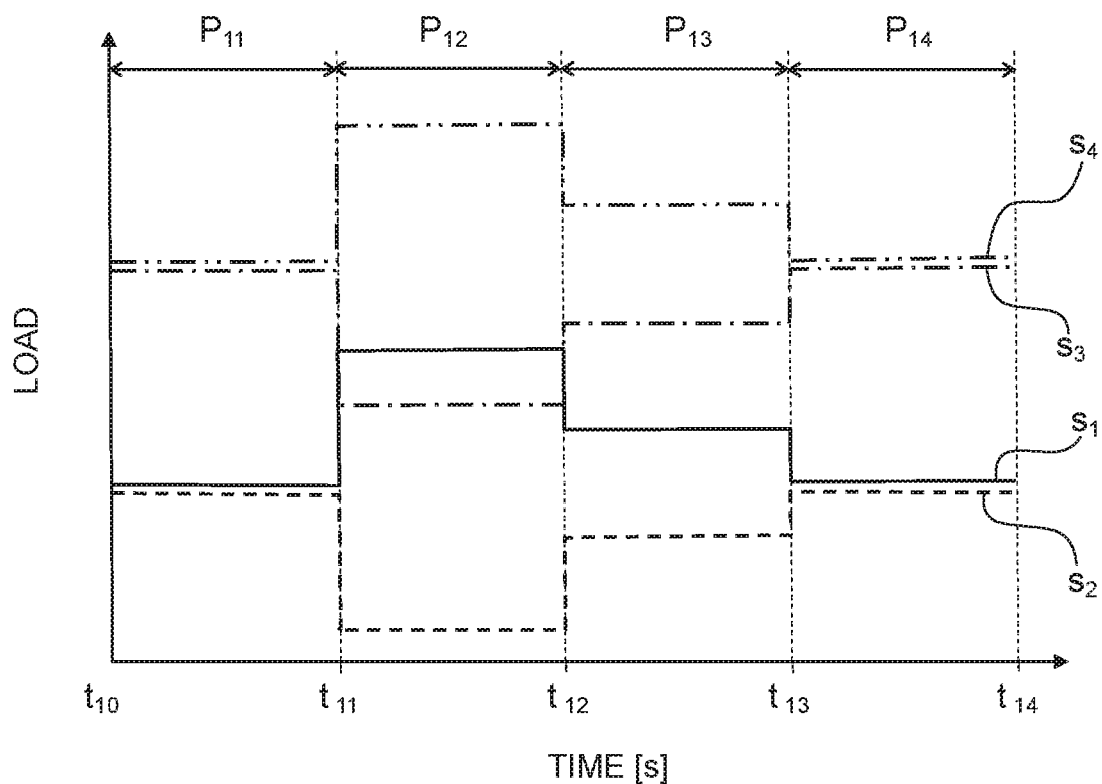
FIG. 5 depicts exemplary load signals fed from the load detectors.

Exemplary load signals are depicted in FIG. 5. FIG. 5 depicts the load signals $s_1$ (solid line), $s_2$ (broken line), $s_3$ (alternate long and short dash line), and $s_4$ (alternate long and two short dashes line) fed from the load detectors 11, 12, 13, 14 as outputted during the period ranging from the time $t_{10}$ to the time $t_{14}$. The following fact has been observed. That is, the subject S lay on his/her back at the central portion of the bed BD as depicted in FIG. 4 during the period ranging from the time $t_{10}$ to the time $t_{11}$ (period $P_{11}$). The subject S moved to the side of the areas I, IV of the bed BD during the period ranging from the time $t_{11}$ to the time $t_{12}$ (period $P_{12}$). The subject S moved to some extent to the central side of the bed BD during the period ranging from the time $t_{12}$ to the time $t_{13}$ (period $P_{13}$) as compared with the period $P_{12}$. The subject S lay on his/her back at the central portion of the bed BD during the period ranging from the time $t_{13}$ to the time $t_{14}$ (period $P_{14}$).

During the period $P_{11}$, the subject S lay on his/her back at the central portion of the bed BD as depicted in FIG. 4. Therefore, during the period $P_{11}$, the signals $s_3$, $s_4$, which are fed from the load detectors 13, 14 arranged on the head side of the subject S, are approximately equal to one another, and the signals $s_1$, $s_2$, which are fed from the load detectors 11, 12 arranged on the foot side of the subject S, are approximately equal to one another.

During the period $P_{12}$, the subject S moved to the side of the areas I, IV of the bed BD. Therefore, during the period $P_{12}$, the signals $s_1$, $s_4$, which are fed from the load detectors 11, 14 arranged in the areas I, IV, exhibit the large load values as compared with the period $P_{11}$, and the signals $s_2$, $s_3$, which are fed from the load detectors 12, 13 arranged in the areas II, III, exhibit the small load values as compared with the period $P_{11}$.

During the period $P_{13}$, the subject S moved to some extent to the central side of the bed BD as compared with the period $P_{12}$. Therefore, during the period $P_{13}$, the signals $s_1$, $s_4$, which are fed from the load detectors 11, 14 arranged in the areas I, IV, exhibit the small load values as compared with the period $P_{12}$, and the signals $s_2$, $s_3$, which are fed from the load detectors 12, 13 arranged in the areas II, III, exhibit the large load values as compared with the period $P_{12}$.

During the period $P_{14}$, the subject S lay on his/her back at the central portion of the bed BD in the same manner as the period $P_{11}$. Therefore, during the period $P_{14}$, the signals $s_1$ to $s_4$, which are provided during the period $P_{14}$, are the same as the signals $s_1$ to $s_4$ provided during the period $P_{11}$.

Figure 6:
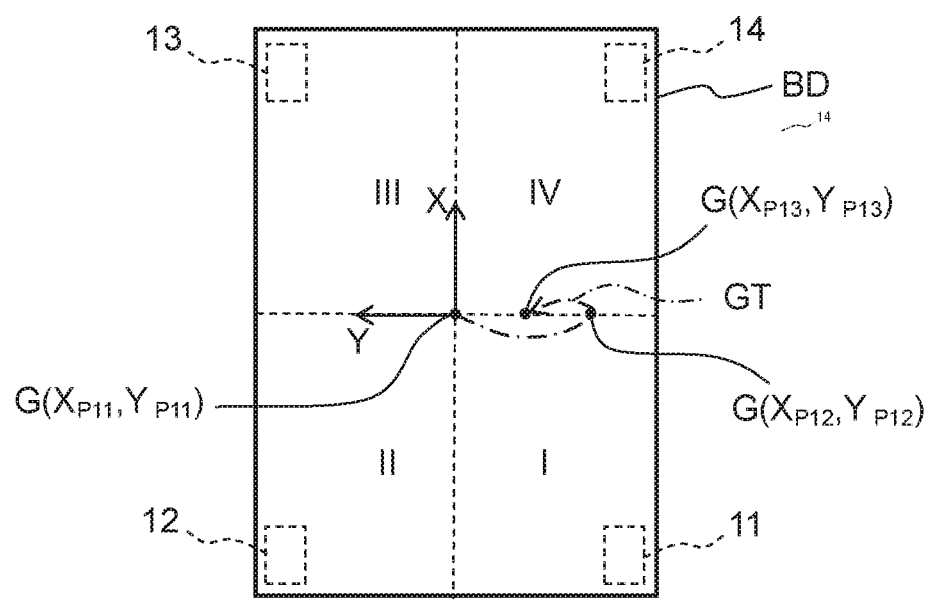
FIG. 6 depicts an exemplary locus (trajectory, path) of the center of gravity (the center of gravity locus) of a subject.

In the center of gravity locus calculating step S02, the center of gravity position calculation unit 31 calculates the position G (X, Y) of the center of gravity G of the subject S on the bed BD at a predetermined period T (for example, a period equal to the sampling period of 5 milliseconds described above) on the basis of the load signals $s_1$ to $s_4$ fed from the load detectors 11 to 14 to obtain the temporal variation of the position of the center of gravity G of the subject S (center of gravity locus GT). In this case, (X, Y) indicates the coordinates on the XY coordinate plane in which X extends in the longitudinal direction of the bed BD and Y extends in the lateral direction of the bed BD while the central portion of the bed BD is the origin (FIG. 6).

The calculation of the position G (X, Y) of the center of gravity G by the center of gravity position calculation unit 31 is performed in accordance with the following operation. That is, G (X, Y) is calculated in accordance with the following expressions assuming that the coordinates of the load detectors 11, 12, 13, 14 are $(X_{11}, Y_{11})$, $(X_{12}, Y_{12})$, $(X_{13}, Y_{13})$, and $(X_{14}, Y_{14})$ respectively, and the detection values of the load detectors 11, 12, 13, 14 are $W_{11}$, $W_{12}$, $W_{13}$, and $W_{14}$ respectively.

$$X = \frac{X_{11} \times W_{11} + X_{12} \times W_{12} + X_{13} \times W_{13} + X_{14} \times W_{14}}{W_{11} + W_{12} + W_{13} + W_{14}}$$ (Numerical expression 1)

-continued $$Y = \frac{Y_{11} \times W_{11} + Y_{12} \times W_{12} + Y_{13} \times W_{13} + Y_{14} \times W_{14}}{W_{11} + W_{12} + W_{13} + W_{14}}$$ (Numerical expression 2)

The center of gravity position calculation unit 31 obtains the temporal variation of the position G (X, Y) of the center of gravity G, i.e., the center of gravity locus GT while calculating the position G (X, Y) of the center of gravity G at the predetermined sampling period T on the basis of the numerical expressions (1) and (2) described above. The obtained center of gravity locus GT is stored, for example, in the storage unit 4.

An example of the center of gravity locus GT calculated by the center of gravity position calculation unit 31 is depicted in FIG. 6. FIG. 6 depicts the positions G ($X_{P11}$, $Y_{P11}$), G ($X_{P12}$, $Y_{P12}$), G ($X_{P13}$, $Y_{P13}$) of the center of gravity G of the subject S on the bed BD at the time $t_{110}$, $t_{120}$, $t_{130}$ included in the periods $P_{11}$, $P_{12}$, $P_{13}$ depicted in FIG. 5 respectively. An arrow of alternate long and short dash line to connect G ($X_{P11}$, $Y_{P11}$), G ($X_{P12}$, $Y_{P12}$), G ($X_{P13}$, $Y_{P13}$) indicates the center of gravity locus GT of the center of gravity G of the subject S moving from the position G ($X_{P11}$, $Y_{P11}$) to G ($X_{P13}$, $Y_{P13}$).

The inventors of the present invention have found out that the center of gravity locus GT of the subject S calculated and obtained by the center of gravity position calculation unit 31 includes the locus of the center of gravity movement due principally to three types of biological activities of the subject S.

The first one is the locus of the center of gravity movement due to a comparatively large body motion along with a torso (body-trunk) motion of the subject S such as a turn-over or the like. In the present invention, such kind of comparatively large body motion is referred to as "large body motion". The large body motion includes, specifically, turn-over, get-up (set up), or the like. If the subject performs a large body motion, then generally speaking, a direction of the subject's body axis (direction in which the backbone of the subject extends) changes.

When the large body motion is defined in view of the manner of the temporal variation of the position of the center of gravity, the large body motion can be defined in general to be the movement of the center of gravity for a relatively long distance exceeding a predetermined distance, which occurs within a predetermined time period. Alternatively, it is also possible to define, on the basis of the difference from the temporal variation of the position of the center of gravity caused by the small body motion as described later on, for example, that the large body motion is the body motion by which the center of gravity is moved, within a predetermined time period, at least nearly predetermined times as greatly as the movement distance of the center of gravity by the small body motion. Further, it is also allowable to define, by comparing with the amplitude of a respiratory oscillation as described later on.

The second one is the locus of the center of gravity movement due to a comparatively small body motion without any torso (body-trunk) motion of the subject S such as a motion of the hand, foot, face, or the like. In the present invention, such kind of comparatively small body motion is referred to as "small body motion". The small body motion includes, specifically for example, only the motion of hand, foot, and/or head or the like. Note that in this specification and the present invention, the "large body motion" and the "small body motion" may be collectively referred to as "body motion".

When the small body motion is defined in view of the manner of the temporal variation of the position of the center of gravity, the small body motion can be defined in general to be the movement of the center of gravity for a relatively short distance within a predetermined time period. Further, it is also allowable to define, by comparing with the amplitude of the respiratory oscillation as described later on. Further, it is also allowable to define that the small body motion is the body motion to cause the movement of the center of gravity for a relatively short distance within a predetermined time period, the movement of the center of gravity not being an oscillation in a constant direction. According to this definition, when an attention is paid to the movement of the center of gravity, it is possible to further clearly distinguish the small body motion from the respiration.

The third one is the locus of the center of gravity movement due to the respiration of the subject. The respiration of human is performed by moving the chest and the diaphragm to expand and shrink the lungs. In this context, when the air is inhaled, i.e., when the lungs are expanded, the diaphragm is lowered downwardly, and the internal organs are also moved downwardly. On the other hand, when the air is expired, i.e., when the lungs are shrunk, the diaphragm is raised upwardly, and the internal organs are also moved upwardly. As a result of the research performed by the inventors of the present invention, it has been found out that in accordance with the movement of the internal organs, the center of gravity G oscillates approximately along the extending direction of the backbone (body axis direction).

Note that in this specification and the present invention, the term "respiratory oscillation (respiratory vibration)" refers to a reciprocating movement of the center of gravity of the subject along the body axis direction, due to the respiration of the subject, while the term "locus of respiratory oscillation (respiratory oscillation locus)" refers to the locus of that respiratory oscillation. Further, the term "respiratory waveform (respiration waveform)" of the subject refers to a waveform depicting the respiratory oscillation in time domain such as, for example, a waveform of the respiratory oscillation shown in a graph of which vertical axis represents the body axis direction and horizontal axis represents time.

In this specification and the present invention, the term "stable body position period" refers to a period in which the subject does not perform the large body motion. The term "stable respiration period" refers to a period, within the stable body position period, in which the subject performs only respirations in a certain position without the small body motion.

Figure 7:
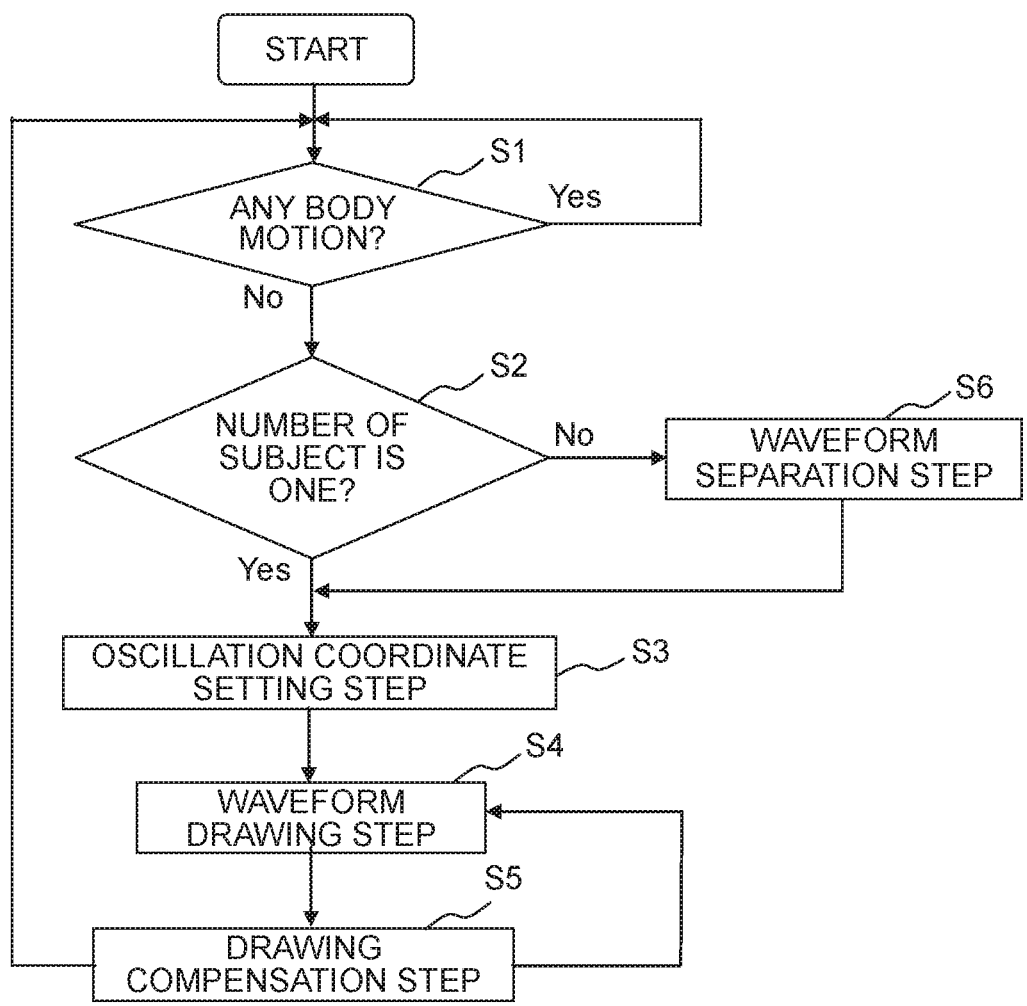
FIG. 7 is a flow chart depicting a waveform drawing method according to the embodiment of the present disclosure.

Next, referring to the flow chart of FIG. 7, it will be described a method for drawing the respiratory waveform of the subject S on the basis of the center of gravity position of the subject S, calculated by the center of gravity position calculating unit 31. First, an outline of an entire process will be explained. The detail of each step will be described later on.

In a body motion determination step S1, a body motion detection unit 32 detects whether or not the subject S on the bed has performed a body motion (the large body motion or the small body motion). If the subject on the bed has performed a body motion (S1: Yes), then the body motion determination step S1 is repeated. If there is no body motion (S1: No), then the process proceeds to a subject number determination step S2.

In the subject number determination step S2, the control unit 3 determines the number of subjects S on the bed BD. If the number of subjects S is one (S2: Yes), then the control unit 3 causes the oscillation coordinate setting unit 34 to set an oscillation coordinate of the respiratory oscillation (the detail of which will be described later on) of the subject S in an oscillation coordinate setting step S3.

If there are a plurality of subjects S (S2: No), then the control unit 3 causes a waveform separation unit 33 to perform a waveform separation step S6. In the waveform separation step S6, the superimposed respiratory oscillations of the plurality of subjects S are separated such that the respiratory oscillation of each of the plurality of subjects S is taken out (extracted). For each of the respiratory oscillations separated and taken out, the control unit 3 causes the oscillation coordinate setting unit 34 to perform the oscillation coordinate setting step S3, so as to set up the oscillation coordinate of the respiratory oscillations of each of the plurality of subjects S.

In a waveform drawing step S4, the waveform drawing unit 35 draws the respiratory waveform of the subject S (or each of the respiratory waveforms of the subjects S if there are a plurality of subjects S) on the basis of the oscillation coordinate set up in the oscillation coordinate setting step S3, and displays the drawn respiratory waveform on the display unit 5.

The control unit 3 causes the drawing compensation unit 36 to perform the drawing compensation step S5, as necessary, such that the display unit 5 reliably continues the display of the respiratory waveform during a period in which the waveform drawing step S4 is performed. If the respiratory waveform drawn in the waveform drawing step S4 has lost its continuity, then the drawing compensation unit 36 first determines whether or not it is possible to compensate the drawing state, and performs a compensation of the drawing state if the compensation is possible. On the other hand, if it is not possible to compensate the drawing state, then the drawing compensation unit 36 notifies the control unit 3 of the fact. In this case, the control unit 3 stops the drawing of the respiratory waveform and returns the process to the body motion determination step S1.

Next, each step for drawing a respiratory waveform of the subject S in accordance with the flow chart of FIG. 7 will be explained using the following case as an example. That is, a case of drawing the respiratory waveform of the subject S in a period in which the number of the subjects S on the bed BD is one and the subject S performs a movement of the center of gravity along a locus depicted in FIG. 8, and FIGS. 9A to 9C.

Figure 8:
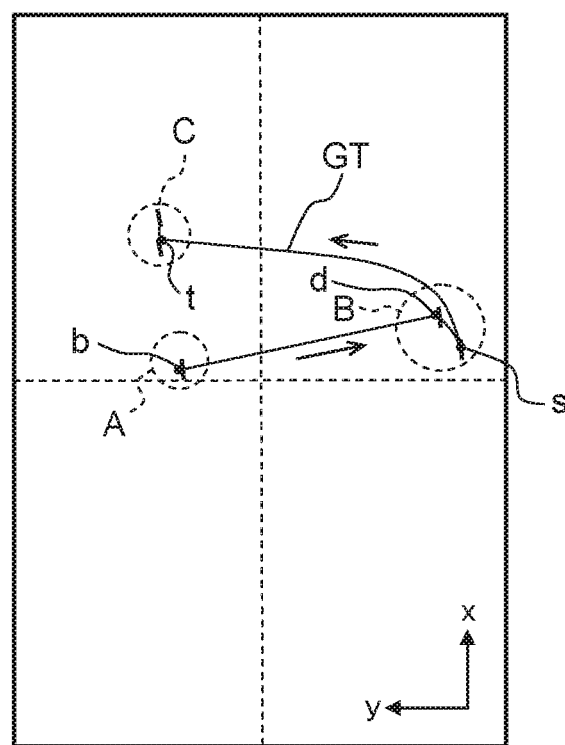
FIG. 8 depicts another exemplary center of gravity locus of the subject.

The center of gravity locus GT depicted in FIG. 8 shows the locus of the center of gravity movement of the subject S over about two minutes, calculated by the center of gravity position calculation unit 31. Note that the arrows indicate the moving direction of the center of gravity G.

During the period in which the movement of the center of gravity G from the point "b" to the point "d" in FIG. 8 and FIGS. 9A and 9B is recorded, it is observed that the subject S turns over and moves from the vicinity of the center of the bed to the vicinity of the left end of the bed (on the left side as viewed from the subject S lying face-up or supine). Further, during the period in which the movement of the center of gravity G from the point "s" to the point "t" in FIG. 8 and FIGS. 9B and 9C is recorded, it is observed that the subject S turns over and moves from the vicinity of the left end of the bed to the vicinity of the center of the bed. The locus of the movement of the center of gravity G from an area A to an area B and the locus of the movement of the center of gravity G from the area B to an area C are loci of the center of gravity movement due to the large body motion along with the torso motion of the subject S.

During the period in which the locus of the center of gravity G from the point "l" to the point "m" in FIG. 9B (an enlarged view of the area B of FIG. 8) is recorded, it is observed that the subject S moves the right arm obliquely downward while lying face-down or prone on the left end of the bed. Further, during the period in which the locus of the center of gravity G from the point "u" to the point "v" in FIG. 9C (an enlarged view of the area C of FIG. 8) is recorded, it is observed that the subject S bends the right arm and moves the hand upward without moving the torso while lying supine. During those periods, the locus of the obliquely downward movement of the center of gravity G and the locus of the upward movement are the loci of the center of gravity movement due to the small body motion along with the arm motion of the subject S.

During the other (remaining) section (period) in which neither the above loci of the center of gravity movement due to the large body motion nor the above loci of the center of gravity movement due to the small body motion is recorded, the center of gravity locus GT oscillates in an up/down direction (an x direction). In this section (period), it is observed that the subject S performs neither the large body motion nor the small body motion, but is sleeping in a certain position. Therefore, in such sections, the reciprocating movement (oscillation) of the center of gravity G is a respiratory oscillation along the body axis direction of the subject S, and its locus is a respiratory oscillation locus.

Note that because the respiratory oscillation occurs along the body axis direction of the subject S, in reality, the respiratory oscillation locus appears on almost one axis with overlap. However, in FIGS. 9A to 9C, for the sake of explanation, the respiratory oscillation locus is drawn such that the locus gradually shifts in a direction orthogonal to the body axis direction.

In the center of gravity locus GT depicted in FIG. 8 and FIGS. 9A to 9C, the period in which the center of gravity locus GT in the sections between the points "a" and "b", between the points "d" and "s", and between the points "t" and "w" is recorded belongs to the stable body position period, wherein the period in which the center of gravity locus GT in the sections between the points "a" and "b", between the points "d" and "l", between the points "m" and "s", between the points "t" and "u", and between the points "v" and "w" is recorded belongs to the stable respiration period.

[Body Motion Determination Step]

In the body motion determination step S1, as described earlier on, the body motion detection unit 32 detects whether or not the subject S on the bed performs a body motion (the large body motion or the small body motion). Specifically, for example, the following method is used.

When the subject S performs the large body motion or the small body motion, a movement of the body brought about thereby gives rise to a far larger change of the center of gravity position than that caused by the movement of internal organs brought about by the respiration of the subject S. In other words, the speed of the center of gravity G movement (the displacement per unit time) due to the large body motion or the small body motion is far larger than the speed of the movement of the center of gravity position due to the respiration of the subject S. Further, the speed of the center of gravity G movement due to the large body motion is larger than the speed of the center of gravity G movement due to the small body motion. Note that, in FIG. 8 and FIGS. 9A to 9C, the respiratory oscillation locus is enlarged for the sake of explanation.

Accordingly, on the basis of the positional change among the center of gravity G of the subject S at each time stored in the storage unit 4, the body motion detection unit 32 calculates the moving speed of the center of gravity G, and determines that the subject S is performing a body motion in a case that the calculated speed is more than a predetermined threshold value, and determines that the subject S is not performing a body motion in a case that the calculated speed is not more than the predetermined threshold value.

When the center of gravity G of the subject S is at the point "c" in FIG. 9B, the subject S is performing the large body motion where the moving speed of the center of gravity G is more than the predetermined threshold value. Therefore, in the body motion determination step S1, the body motion detection unit 32 determines that there is a body motion, so that the control unit 3 returns the process to the body motion detection step S1.

Next, if the center of gravity G of the subject S reaches the point "d" in FIGS. 8 and 9B, then the subject S is finished with the large body motion, so that the moving speed of the center of gravity G is not more than the predetermined threshold value. Therefore, in the body motion detection step S1, the body motion detection unit 32 determines that there is no body motion, and thus the control unit 3 lets the process proceed to the subject number determination step S2. Note that whether or not there is a body motion may be determined by another method on the basis of the definition of the large body motion and/or the small body motion.

[Subject Number Determination Step]

In the subject number determination step S2, the control unit (a subject number determination unit) 3 determines whether the number of the subject S on the bed BD is one or not. Specifically, for example, the following method is used.

As described above, the position of the center of gravity G of the subject S oscillates on the bed BD according to the respiration of the subject S on the bed BD. The load signals $s_1$ to $s_4$ fed from the load detectors 11 to 14 arranged respectively under the four legs of the bed BD also vary with cycle (period) according to the respiration of the subject S on the bed, respectively. Therefore, if at least one of the load signals $s_1$ to $s_4$ undergoes a Fourier transform to obtain the frequency spectrum for the frequency range corresponding to the respiration (from about 0.2 Hz to about 0.33 Hz. Hereinbelow, it will be referred to as the respiration range), then the peak frequency will appear at the position corresponding to the frequency of the respiration of the subject S.

Here, the respiration cycle (respiratory cycle) differs depending on the sex (gender), physique (physical constitution), lung capacity (vital capacity) and the like of the subject S. Therefore, if there are a plurality of subjects S on the bed BD, then the same number of different peak frequencies, as that of subjects S, appear in the frequency spectrum over the respiration range.

Therefore, the control unit 3 causes the waveform separation unit 33 to perform the Fourier analysis of at least one of the load signals $s_1$ to $s_4$ fed from the load detecting unit 1 so as to calculate the frequency spectrum over the respiration range, and determine that there is one subject S if one peak frequency appears or determines that there are a plurality of subjects S if a plurality of peak frequencies appear. Here, as described earlier on, there is one subject S on the bed BD so that only one peak frequency appears; therefore the control unit 3 determines that there is one subject S (S2: Yes).

[Oscillation Coordinate Setting Step and Waveform Drawing Step]

In the oscillation coordinate setting step S3, the oscillation coordinate setting unit 34 sets up the oscillation coordinate for the respiratory oscillation included in the center of gravity locus GT of the subject S, and calculates the displacement necessary for drawing the respiratory waveform on the basis of the set oscillation coordinate. In the waveform drawing step S4, the waveform drawing unit 35 draws the respiratory waveform of the subject S on the basis of the displacement calculated by the oscillation coordinate setting unit 34.

In this specification and the present invention, setting up the oscillation coordinate means setting the "oscillation origin" indicating the oscillation center of the respiratory oscillation, and the direction of the oscillation axis indicating the oscillation direction of the respiratory oscillation (the direction in which the body axis of the subject S extends).

Figure 10:
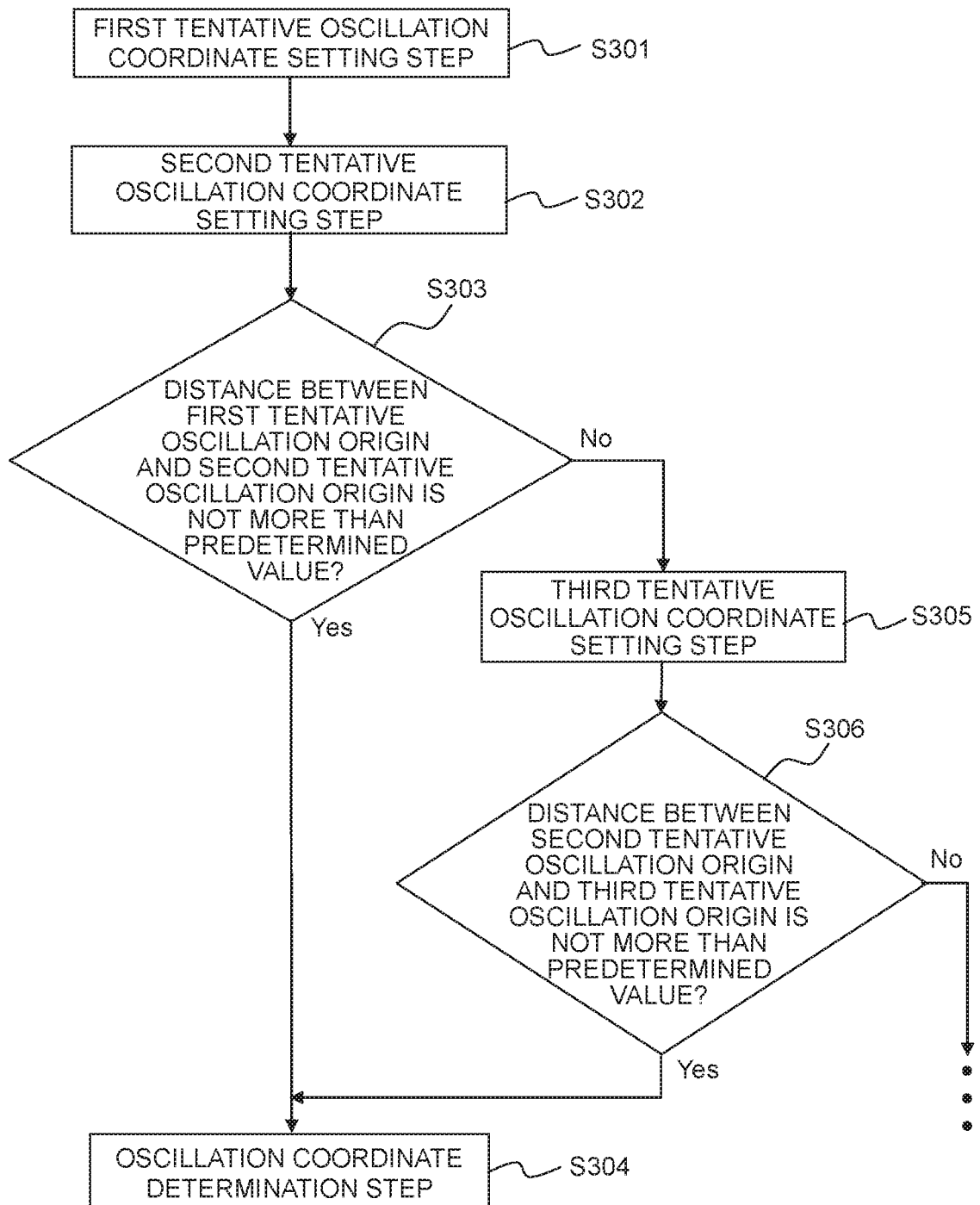
FIG. 10 is a flow chart depicting a procedure of an oscillation coordinate setting step.

As depicted in FIG. 10, the oscillation coordinate setting step S3 includes, principally, a first tentative (provisional) oscillation coordinate setting step S301, a second tentative oscillation coordinate setting step S302, a tentative oscillation origin comparison step S303, and a oscillation coordinate determination step S304.

The waveform drawing step S4 is performed partially in parallel to the oscillation coordinate setting step S3. In the waveform drawing step S4, the waveform drawing unit 35 draws a tentative respiratory waveform of the subject S using distance information outputted from the oscillation coordinate setting unit 34 in the first tentative oscillation coordinate setting step S301 and the second tentative oscillation coordinate setting step S302, and displays the same on the display unit 5. Further, in the waveform drawing step S4, the waveform drawing unit 35 draws the definite (established, or regular) respiratory waveform of the subject S using displacement information outputted from the oscillation coordinate setting unit 34 on the basis of the oscillation coordinate determined in the oscillation coordinate determination step S304, and displays the same on the display unit 5.

Note that in this specification, the term "tentative respiratory waveform" means a respiratory waveform drawn on the basis of a tentative oscillation coordinate, i.e., a tentative oscillation origin and a tentative oscillation axis before the oscillation coordinate (i.e. the oscillation origin O and the oscillation axis A) is determined in the oscillation coordinate determination step S304. The term "definite (established, or regular) respiratory waveform" means the respiratory waveform depicted on the basis of the oscillation origin O and the oscillation axis A after the oscillation coordinate is determined in the oscillation coordinate determination step S304.

Hereinbelow, following the flow chart of FIG. 10, an explanation will be made about setting up of the oscillation coordinate for the subject S performed by the oscillation coordinate setting unit 34, and drawing of a respiratory waveform of the subject S performed by the waveform drawing unit 35.

(First Tentative Oscillation Coordinate Setting Step S301)

Figure 11A:
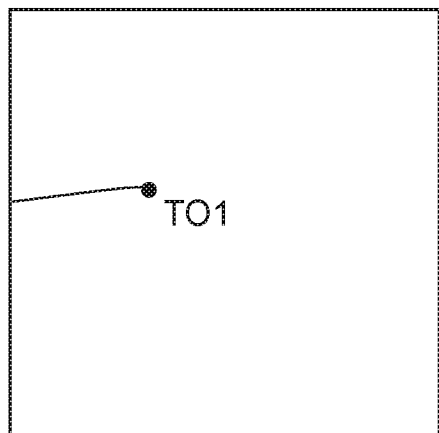
FIG. 11A is an illustrative view for explaining a method for determining an oscillation origin and an oscillation axis, depicting an example of a first tentative (provisional) oscillation origin set by the method.
Figure 11B:
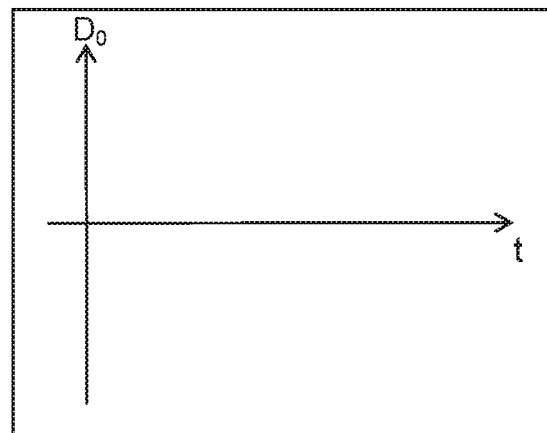
FIG. 11B depicts a pattern of a tentative respiratory waveform drawn by a waveform drawing unit up to the point of time corresponding to FIG. 11A.
Figure 12A:
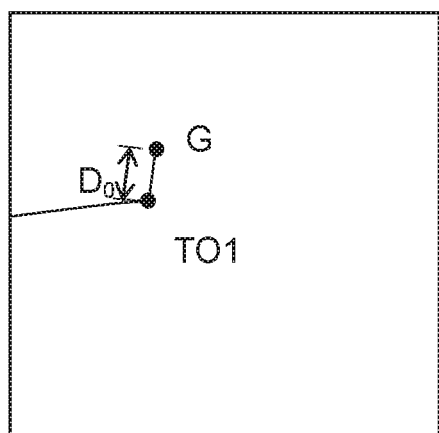
FIG. 12A is an illustrative view for explaining the method for determining the oscillation origin and the oscillation axis, depicting an example of a distance between the first tentative oscillation origin and the center of gravity.
Figure 12B:
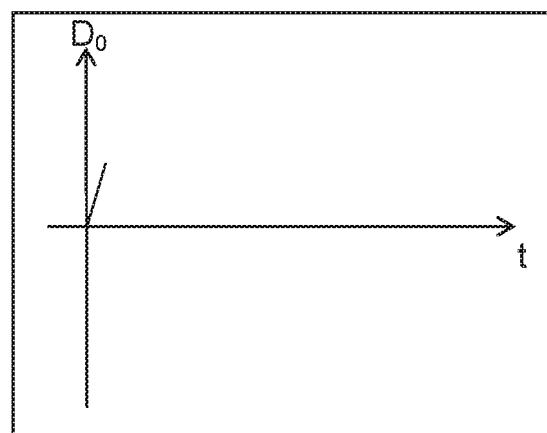
FIG. 12B depicts a pattern of the tentative respiratory waveform drawn by the waveform drawing unit up to the point of time corresponding to FIG. 12A.

As depicted in FIG. 11A, the oscillation coordinate setting unit 34 takes the point, at which it is determined that there is no longer any body motion in the body motion determination step S1, as a first tentative oscillation origin TO1 (an example of the initial origin). This point corresponds to the point "d" on the center of gravity locus GT exemplified in FIG. 9B. At this point of time, the waveform drawing unit 35 has not yet started drawing of the respiratory waveform (FIG. 11B).

After the first tentative oscillation origin TO1 is set, the oscillation coordinate setting unit 34 sequentially calculates a straight distance $D_0$ (FIG. 12A and FIG. 13A) between the first tentative oscillation origin TO1 and the center of gravity G moving therefrom, and outputs the calculated values to the waveform drawing unit 35.

The waveform drawing unit 35 plots the received values of the straight distance $D_0$ on a graph with the horizontal axis as the time axis (axis t) and with the vertical axis as the distance axis (axis $D_0$) so as to draw a tentative respiratory waveform of the subject S (FIG. 12B and FIG. 13B), and displays the same on the display unit 5.

Figure 13A:
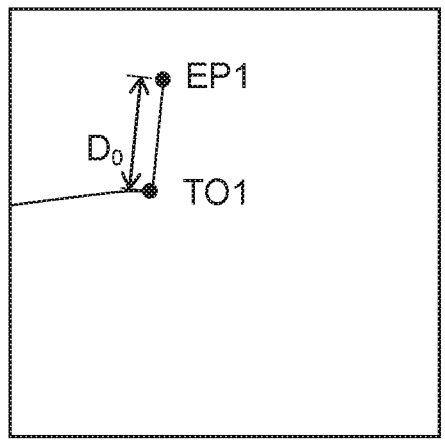
FIG. 13A is an illustrative view for explaining the method for determining the oscillation origin and the oscillation axis, depicting an example of a first extreme point set by the method.
Figure 13B:
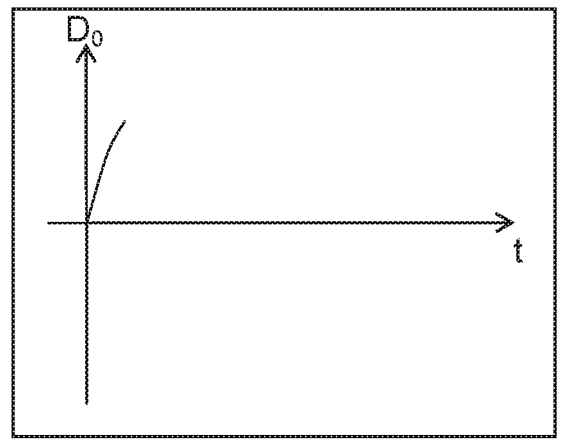
FIG. 13B depicts a pattern of the tentative respiratory waveform drawn by the waveform drawing unit up to the point of time corresponding to FIG. 13A.

The oscillation coordinate setting unit 34 observes the value of the distance $D_0$ between the first tentative oscillation origin TO1 and the center of gravity G, finds the point at which the distance $D_0$ becomes maximum, and defines (set) this point as the first extreme point (extremal point) EP1 (FIG. 13A). At the first extreme point EP1, the change of the distance $D_0$ turns from increase to decrease. The first extreme point EP1 corresponds to the point "e" on the center of gravity locus GT exemplified in FIG. 9B.

Figure 14A:
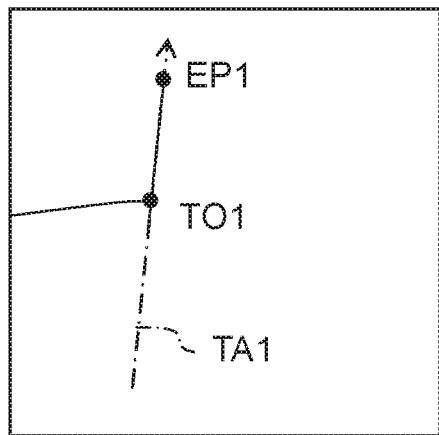
FIG. 14A is an illustrative view for explaining the method for determining the oscillation origin and the oscillation axis, depicting an example of a first tentative oscillation axis set by the method.
Figure 14B:
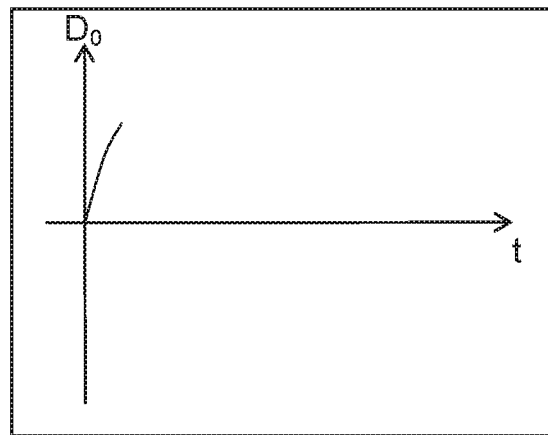
FIG. 14B depicts a pattern of the tentative respiratory waveform drawn by the waveform drawing unit up to the point of time corresponding to FIG. 14A.
Figure 15A:
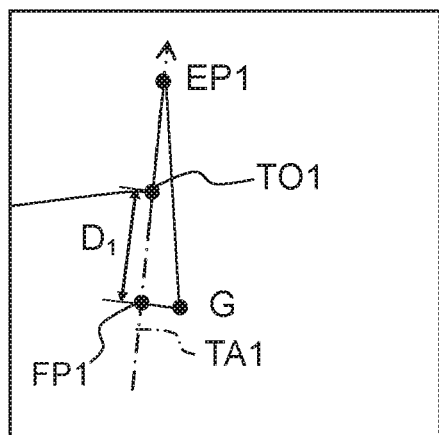
FIG. 15A is an illustrative view for explaining the method for determining the oscillation origin and the oscillation axis, depicting an example of a distance between the first tentative oscillation origin and the foot of a perpendicular line drawn from the center of gravity down to the first tentative oscillation axis.
Figure 15B:
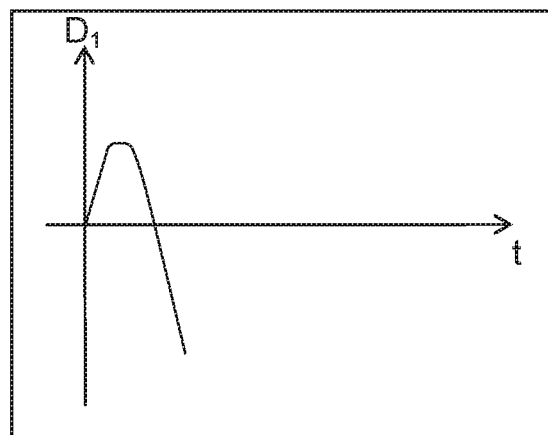
FIG. 15B depicts a pattern of the tentative respiratory waveform drawn by the waveform drawing unit up to the point of time corresponding to FIG. 15A.
Figure 16A:
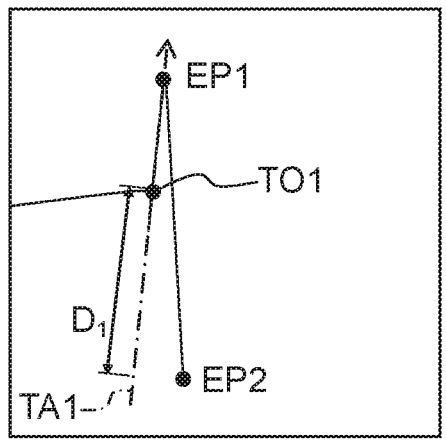
FIG. 16A is an illustrative view for explaining the method for determining the oscillation origin and the oscillation axis, depicting an example of a second extreme point set by the method.
Figure 16B:
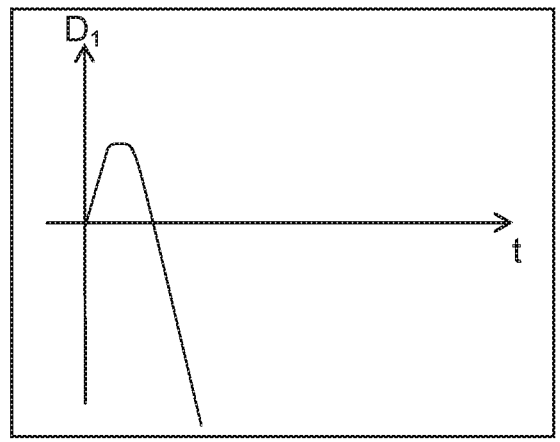
FIG. 16B depicts a pattern of the tentative respiratory waveform drawn by the waveform drawing unit up to the point of time corresponding to FIG. 16A.

Next, as shown in FIG. 14A, the oscillation coordinate setting unit 34 calculates the axis linking the first tentative oscillation origin TO1 and the first extreme point EP1, and sets the same as a first tentative oscillation axis TA1 and sets the first tentative oscillation origin TO1 as the origin of the first tentative oscillation axis TA1. That is, the oscillation coordinate setting unit 34 tentatively sets the oscillation direction of the respiratory oscillation started from the first tentative oscillation origin TO1, i.e., the oscillation axis direction (the direction of the body axis) of that respiratory oscillation as the direction of the first tentative oscillation axis TA1, and tentatively sets the oscillation origin of that respiratory oscillation as the first tentative oscillation origin TO1.

Further, the oscillation coordinate setting unit 34 sets the side of the first tentative oscillation origin 101 to the first extreme point EP1 (a side of the first tentative oscillation origin TO1 at which the first extreme point EP1 exists) as the positive side of the first tentative oscillation axis TA1 and the other side as the negative side of the first tentative oscillation axis TA1.

(Second Tentative Oscillation Coordinate Setting Step S302)

In the second tentative oscillation coordinate setting step S302, the oscillation coordinate setting unit 34 sequentially calculates a distance $D_1$ between the first tentative oscillation origin TO1 and a foot FP1 of a perpendicular line drawn from the center of gravity G moving from the first extreme point EP1 down to the first tentative oscillation axis TA1, and sends the calculated values to the waveform drawing unit 35. Then, based on the received calculation values, the waveform drawing unit 35 draws a tentative respiratory waveform of the subject S (FIG. 15B and FIG. 16B), and displays the same on the display unit 5.

Further, the oscillation coordinate setting unit 34 observes the distance $D_1$ (FIG. 15A, FIG. 15B, FIG. 16A and FIG. 16B), finds the point at which the distance $D_1$ becomes maximum on the negative side, and defines (set) this point as the second extreme point EP2. At the second extreme point EP2, the change of the distance $D_1$ turns from increase to decrease. The second extreme point EP2 corresponds to the point "f" on the center of gravity locus GT exemplified in FIG. 9B. Note that instead of specifying the second extreme point by using a projection component, of the distance between the center of gravity G and the first tentative oscillation origin TO1, onto the first tentative oscillation axis TA1 as explained above, the second extreme point EP2 may be specified by using the straight distance between the center of gravity G and the first tentative oscillation origin TO1.

Figure 17A:
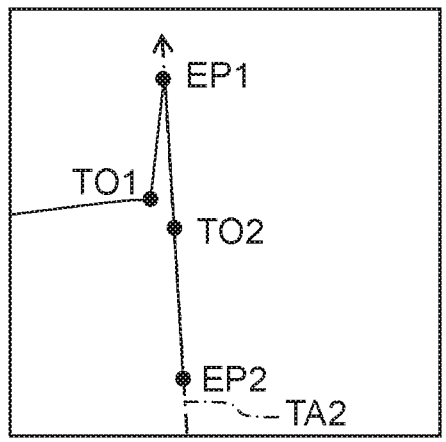
FIG. 17A is an illustrative view for explaining the method for determining the oscillation origin and the oscillation axis, depicting an example of a second tentative oscillation origin and a second tentative oscillation axis set by the method.
Figure 17B:
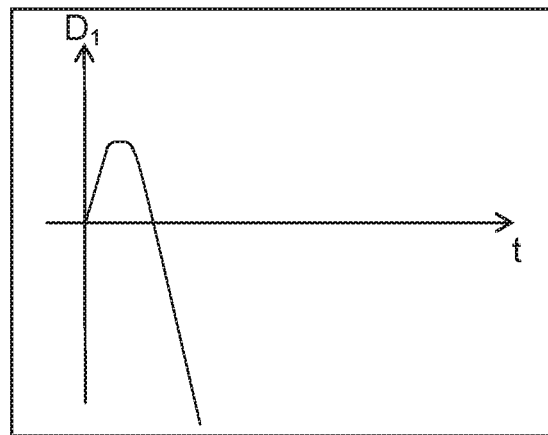
FIG. 17B depicts a pattern of the tentative respiratory waveform drawn by the waveform drawing unit up to the point of time corresponding to FIG. 17A.

Next, as shown in FIG. 17A, the oscillation coordinate setting unit 34 calculates the axis linking the first extreme point EP1 and the second extreme point EP2, and sets the same as a second tentative oscillation axis TA2 (the tentative oscillation axis), and sets the middle point between the first extreme point EP1 and the second extreme point EP2 as a second tentative oscillation origin TO2 (the tentative oscillation origin). That is, the oscillation coordinate setting unit 34 tentatively resets the oscillation axis direction (the direction of the body axis) of the respiratory oscillation started from the first tentative oscillation origin TO1 as the direction of the second tentative oscillation axis TA2, and tentatively resets the oscillation origin of that respiratory oscillation as the second tentative oscillation origin TO2. Further, referring to the positive direction and the negative position of the first tentative oscillation axis TA1, the oscillation coordinate setting unit 34 sets one side of the second tentative oscillation origin TO2 as the positive side of the second tentative oscillation axis TA2 and sets the other side of the second tentative oscillation origin TO2 as the negative side of the second tentative oscillation axis TA2.

(Tentative Oscillation Origin Comparison Step S303)

Next, the oscillation coordinate setting unit 34 calculates the distance between the first tentative oscillation origin TO1 set in the first tentative oscillation coordinate setting step S301, and the second tentative oscillation origin TO2 set in the second tentative oscillation coordinate setting step S302, and determines whether or not the calculated distance is not more than a predetermined value. It is possible to set the predetermined value, for example, as 10% of the distance between the first extreme point EP1 and the second extreme point EP2.

(Oscillation Coordinate Determination Step S304)

Figure 18A:
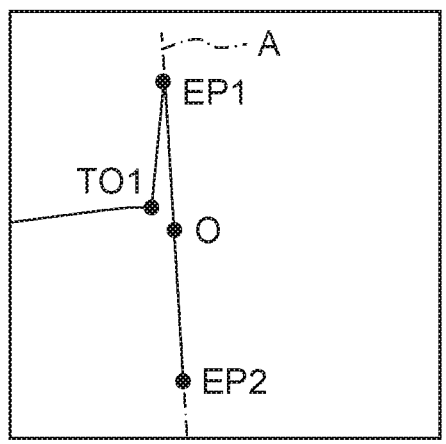
FIG. 18A is an illustrative view for explaining the method for determining the oscillation origin and the oscillation axis, depicting an example of an oscillation origin and an oscillation axis set by the method.
Figure 18B:
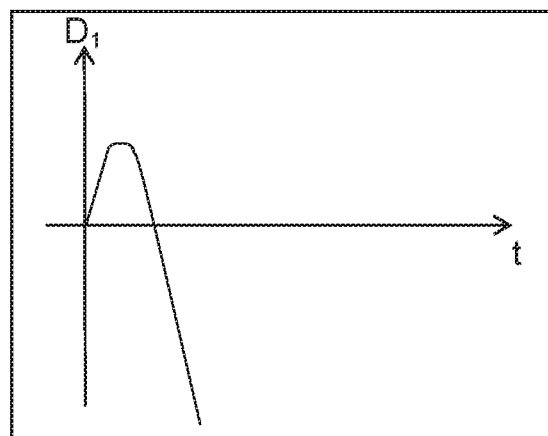
FIG. 18B depicts a pattern of the tentative respiratory waveform drawn by the waveform drawing unit up to the point of time corresponding to FIG. 18A.

As a result of the comparison, if the distance between the first tentative oscillation origin TO1 and the second tentative oscillation origin TO2 is not more than the predetermined value (S303: Yes), then the oscillation coordinate setting unit 34 determines to let the second tentative oscillation origin TO2 be the oscillation origin O of the respiratory oscillation as depicted in FIG. 18A, and to let the second tentative oscillation axis TA2 be the oscillation axis A of the respiratory oscillation, so as to determine the oscillation coordinate. That is, the oscillation coordinate setting unit 34 determines that the center of gravity G of the subject S whose body axis are positioned along the direction of the oscillation axis A is oscillating along the oscillation axis A with the oscillation origin O as the oscillation center, due to the respiration of the subject S.

On the other hand, as a result of the comparison, if the distance between the first tentative oscillation origin TO1 and the second tentative oscillation origin TO2 is more than the predetermined distance (S303: No), then the oscillation coordinate setting unit 34 performs a third tentative oscillation coordinate setting step S305 and a tentative oscillation origin comparison step S306.

In the third tentative oscillation coordinate setting step S305, in the same manner as in the second tentative oscillation coordinate setting step S302, the oscillation coordinate setting unit 34 observes the distance between the second tentative oscillation origin TO2 and the foot of a perpendicular line drawn from the center of gravity G down to the second tentative oscillation axis TA2, finds the point at which the distance becomes maximum on the positive side, and sets this point as the third extreme point. Next, the oscillation coordinate setting unit 34 calculates the axis linking the second extreme point EP2 and the third extreme point, sets the same as a third tentative oscillation axis (an updated tentative oscillation axis), and sets the middle point between the second extreme point EP2 and the third extreme point as the third tentative oscillation origin TO3 (an updated tentative oscillation origin).

In the tentative oscillation origin comparison step S306, in the same manner as in the tentative oscillation origin comparison step S303, the oscillation coordinate setting unit 34 calculates the distance between the second tentative oscillation origin TO2 set in the second tentative oscillation coordinate setting step S302 and the third tentative oscillation origin TO3 set in the third tentative oscillation coordinate setting step S305, and determines whether or not the calculated distance is not more than a predetermined value. As a result of the comparison, in a case that the distance between the second tentative oscillation origin TO2 and the third tentative oscillation origin TO3 is not more than the predetermined value (S306: Yes), then the oscillation coordinate setting unit 34 determines to let the third tentative oscillation origin TO3 be the oscillation origin O of the respiratory oscillation, and to let the third tentative oscillation axis TA3 be the oscillation axis A of the respiratory oscillation (the oscillation coordinate determination step S304). In a case that the distance between the second tentative oscillation origin TO2 and the third tentative oscillation origin TO3 is more than the predetermined value (S306: No), then the oscillation coordinate setting unit 34 repeats the Nth tentative oscillation coordinate setting step (N=4, 5, 6 . . . ) and the tentative oscillation origin comparison step, in the same manner, until the oscillation coordinate is determined.

Figure 19A:
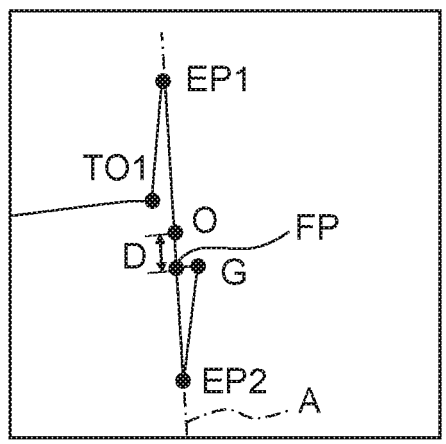
FIG. 19A is an illustrative view for explaining the method for drawing a respiratory waveform by using determined oscillation origin and determined oscillation axis, depicting an example of a distance between the oscillation origin and the foot of a perpendicular line drawn from the center of gravity down to the oscillation axis.

After determining the oscillation origin O and the oscillation axis A in the oscillation coordinate determination step S304, the oscillation coordinate setting unit 34 sequentially calculates, as depicted in FIG. 19A, the distance D between the oscillation origin O and the foot of a perpendicular line drawn from the center of gravity G down to the oscillation axis A, and sends the calculated values as the displacement of the respiratory waveform to the waveform drawing unit 35. On the basis of the received values of displacement, the waveform drawing unit 35 draws the definite respiratory waveform (FIG. 19B) and displays the same on the display unit 5.

Figure 19B:
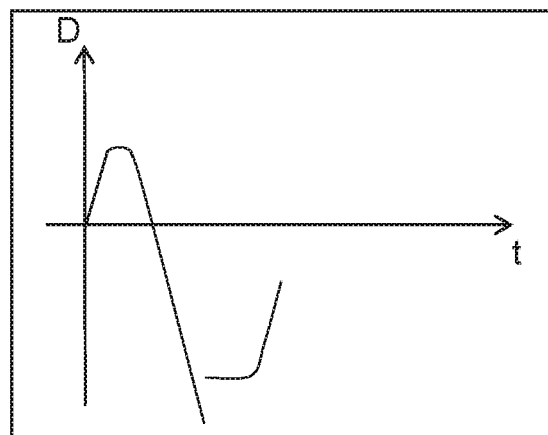
FIG. 19B depicts a pattern of the tentative respiratory waveform and a pattern of a definite respiratory waveform drawn by the waveform drawing unit up to the point of time corresponding to FIG. 19A.

In many cases, there is a difference in the position of the oscillation origin between the determined oscillation coordinate and the tentative oscillation coordinate set immediately therebefore. Therefore, when starting to draw the respiratory waveform on the basis of the determined oscillation coordinate, as depicted in FIG. 19B, a slight deviation may arise between the definite respiratory waveform drawn anew and the tentative respiratory waveforms drawn so far. The deviation may be eliminated by redrawing the drawn tentative respiratory waveform while correcting it on the basis of the difference between the tentative oscillation coordinate and the determined oscillation coordinate.

[Drawing Compensation Step]

Figure 20:
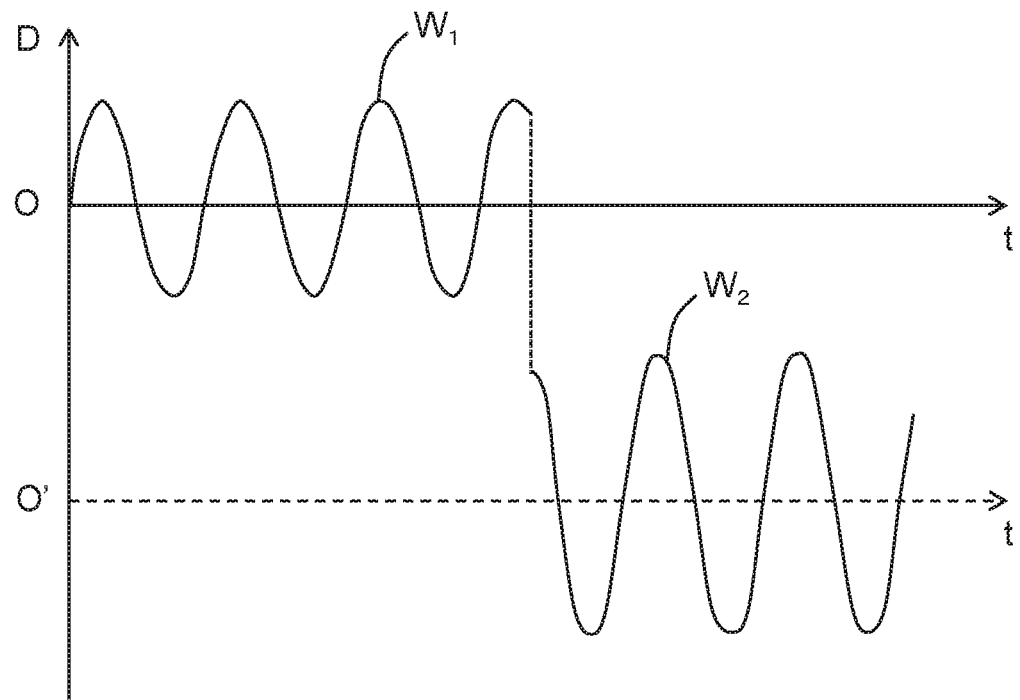
FIG. 20 is a graph illustrating an exemplary respiratory waveform of the subject. In the graph, a respiratory waveform after a body motion of the subject is shifted from a respiratory waveform before the body motion in a direction of an oscillation axis due to a shift of a position of the center of gravity of the subject caused by the body motion.

Here, if the subject S on the bed brings about the small body motion amid the drawing of the respiratory waveform in the waveform drawing step S4, then due to this small body motion, the respiratory waveform shifts in the oscillation axis direction. As depicted in FIG. 9B for example, if the small body motion arises after the stable respiration period from the point "d" to the point "l" and then the stable respiration period continues from the point "m" to the point "s", then as depicted in FIG. 20, a respiratory waveform $W_2$ after the small body motion shifts in the direction of the oscillation axis A set in the oscillation coordinate setting step S3, with respect to a respiratory waveform $W_1$ before that small body motion. Then, depending on the shifted length, possibly, the respiratory waveform $W_2$ after the small body motion cannot be drawn within the displayable range of the display unit 5. In such a case, according to the present disclosure, the drawing compensation unit 36 corrects the drawing position by the following method.

Figure 21:
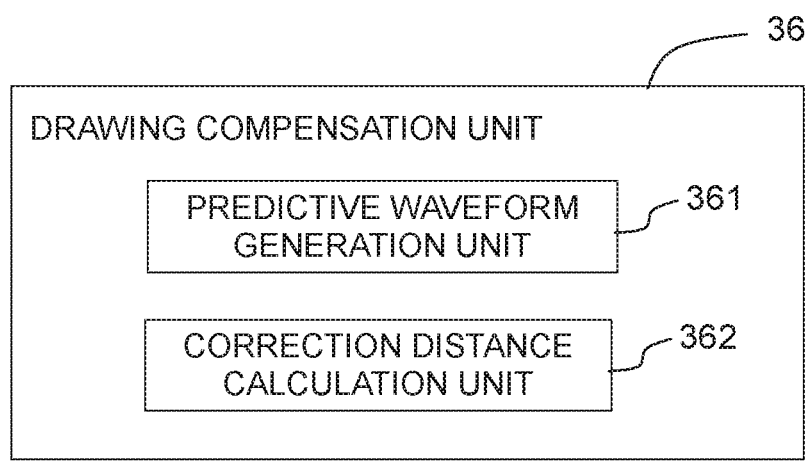
FIG. 21 is a block diagram depicting a detailed configuration of a drawing compensation unit.
Figure 22:
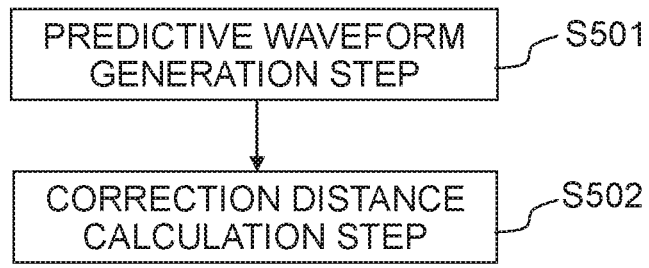
FIG. 22 is a flow chart depicting a procedure of a drawing compensation step.

As depicted in FIG. 21, the drawing compensation unit 36 has a predictive waveform generation unit 361 and a correction distance calculation unit 362. Further, in the drawing compensation step S5, the drawing compensation unit 36 performs a predictive waveform generation step S501 and a correction distance calculation step S502, as depicted in FIG. 22. In the following, the predictive waveform generation step S501 and the correction distance calculation step S502 performed by the drawing compensation unit 36 will be explained.

Figure 23:
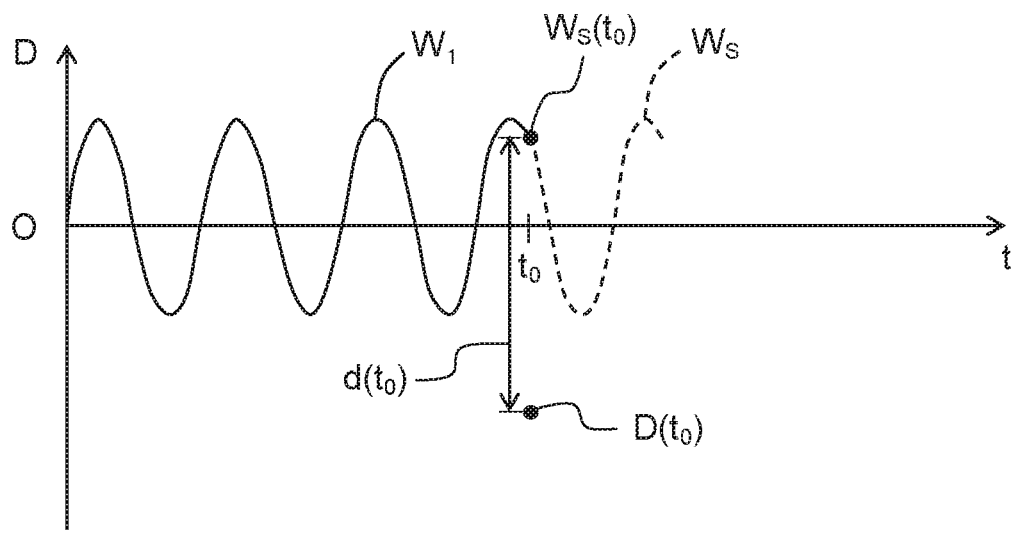
FIG. 23 is an illustrative view for explaining a method for drawing compensation.

In the predictive waveform generation step S501, the predictive waveform generation unit 361 of the drawing compensation unit 36 generates (duplicate) the latest one period of the respiratory waveform $W_1$ already drawn on the display unit 5, for example, as a predictive waveform $W_s$, and draws the predictive waveform $W_s$ on the display unit 5 such that predictive waveform $W_s$ is continuous with the respiratory waveform $W_1$ (FIG. 23. However, the predictive waveform $W_s$ may not be drawn on the display unit 5). Note that in this embodiment, the respiratory waveform $W_1$ is drawn with a solid line while the predictive waveform $W_s$ is drawn with a dotted line so as to distinguish one from the other.

Next, in the correction distance calculation step S502, as depicted in FIG. 23, the correction distance calculation unit 362 of the drawing compensation unit 36 calculates a distance $d(t_0)$ between a point on the predictive waveform $W_s$ at the current sampling time $t_0$ (to be referred to below as predicted point $W_s(t_0)$) and a plot point of the distance D at the current sampling time $t_0$ (to be referred to below as measured point $D(t_0)$). Then, the correction distance calculation unit 362 determines whether or not the distance $d(t_0)$ exceeds a first threshold value $Th_1$ or a second threshold value $Th_2$ larger than the first threshold value $Th_1$. Here, the first threshold value $Th_1$ and the second threshold value $Th_2$ may be appropriately set depending on the size of the display area of the display unit 5. If the distance $d(t_0)$ is smaller than the first threshold value $Th_1$, then the control unit 3 determines that there is no body motion, and causes the waveform drawing step S4 to be performed. Then, in the waveform drawing step S4, the waveform drawing unit 35 continues to draw the respiratory waveform on the basis of the measured point $D(t_0)$ without correcting the drawing position. If the distance $d(t_0)$ is not less than the first threshold value $Th_1$ and not more than the second threshold value $Th_2$, then the control unit 3 determines that the small body motion has arisen, and causes the waveform drawing step S4 to be performed along with a compensation operation in the following manner. That is, the waveform drawing unit 35 moves or offsets the measured point $D(t_0)$ through the distance $d(t_0)$ in the direction of the oscillation axis A. That is, the distance $d(t_0)$ per se is used as the correction distance. If the distance $d(t_0)$ is larger than the second threshold value $Th_2$, then the control unit 3 determines that the large body motion has arisen, and causes the body motion determination step S1 to be performed again.

In this manner, in the drawing compensation step S5, even if the small body motion arises amid the drawing of the respiratory waveform, it is still possible to continuously draw the respiratory waveforms before and after the small body motion within the display range of the display unit 5. Further, if the large body motion arises, the oscillation coordinate is set up again, and then, it is possible to perform the waveform drawing through the process as described above.

Next, following the flow chart of FIG. 7, an explanation will be made about a step of drawing respiratory waveforms of a plurality of subjects S (two persons) on the bed BD, focusing on the difference from the step of drawing the respiratory waveform of a single subject S described above.

In the body motion determination step S1, in the same manner as the case in which the number of the subject is one, whether or not there is a body motion of the subject S is determined on the basis of the moving speed of the center of gravity G on the bed BD. Here, when there are a plurality of subjects S, only one position of the center of gravity G appears as the overall center of gravity position of the plurality of subjects S. Therefore, the control unit 3 determines there is no body motion of the subjects S, in a case that the body motions of all of the plurality of subjects S disappeared.

Next, in the subject number determination step S2, as described earlier on, the waveform separation unit 33 performs the Fourier transform of at least one of the load signals $s_2$ to $s_4$ and obtains the frequency spectrum over the respiration range (from about 0.2 Hz to about 0.33 Hz).

Figure 24:
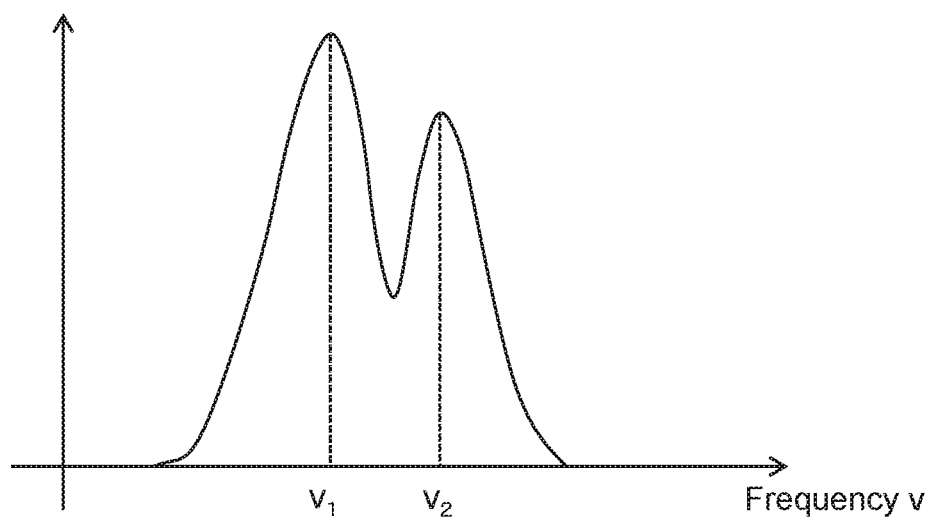
FIG. 24 is an exemplary frequency spectrum of a load signal in a frequency range corresponding to a frequency of respiration.

When there are two subjects S, two peak frequencies appear, such as the peaks appearing in a frequency $v_1$ and a frequency $v_2$ depicted in FIG. 24 for example. On the basis of that, the control unit 3 determines that there are a plurality of subjects S (S2: No).

[Waveform Separation Step]

If a plurality of peak frequencies are specified in the subject number determination step S2, then in the waveform separation step S6, the waveform separation unit 33 obtains the load component of each of the load signals for each of the specified frequencies. It is possible to obtain those load components by way of, for example, a bandpass filter processing for each of the load signals $s_1$ to $s_4$. For example, when the two peak frequencies $v_1$, $v_2$ are specified in the subject number determination step S2, the waveform separating unit 33 obtains four load components $s_{11}$, $s_{21}$, $s_{31}$, $s_{41}$ corresponding to the peak frequency $v_1$ and four load components $s_{12}$, $s_{22}$, $s_{32}$, $s_{42}$ corresponding to the peak frequency $v_2$. Then, the waveform separation unit 33 outputs the four load components corresponding to the peak frequency $v_1$ and the four load components corresponding to the peak frequency $v_2$, to the center of gravity position calculating unit 31. The center of gravity position calculating unit 31 calculates, in the same manner as in the center of gravity locus calculating step S02, the center of gravity position and the center of gravity locus corresponding to each of the peak frequencies $v_1$, $v_2$ (that is, to each of the subjects S) on the basis of the four load components inputted from the waveform separating unit 33.

After the center of gravity locus is found for each of the plurality of subjects S in the waveform separation step S6, on the basis of the center of gravity locus of each of the plurality of subjects S, the oscillation coordinate setting step S3, the waveform drawing step S4, and the drawing compensation step S5 are performed. The details thereof were just as described earlier on in the exemplary case of the one subject S.

The effects of the biological information monitoring system 100 of this embodiment is summarized as follows.

In the biological information monitoring system 100 of this embodiment, because the respiratory waveform is drawn on the basis of a temporal change of the center of gravity position of the subject S, it is possible to present an almost real-time respiratory waveform of the subject S.

Further, in the biological information monitoring system 100 of this embodiment, the oscillation coordinate setting unit 34 first sets a tentative oscillation origin right after the subject S enters into the stable respiration period, and then starts calculating the distance $D_0$ of the center of gravity position therefrom. The waveform drawing unit 35 starts drawing a respiratory waveform on a tentative coordinate system on the basis of the calculated value of the distance $D_0$, before the oscillation coordinate is set. Therefore, it is possible to display the respiratory waveform on the display unit 5 almost right after the large body motion or the small body motion is ended.

Because of that, it is possible to present the respiratory waveform at an earlier stage compared to a case in which the drawing of the respiratory waveform is started after a sampling, in the stable respiration period, of information on a considerable number of center of gravity positions (information corresponding to a plurality of periods of oscillations) and a determination of an oscillation axis and an oscillation origin by applying a calculation process to a locus of the sampled center of gravity positions. Hence, it is possible to observe a real-time respiratory waveform with a restrained time lag.

With the biological information monitoring system 100 of this embodiment, in the drawing compensation step S5, the predictive waveform $W_s$ is generated on the basis of a previous respiratory waveform(s), and the drawing position of the measured point $D(t_0)$ is corrected depending on the distance $d(t_0)$ between the measured point $D(t_0)$ and the predicted point $W_s(t_0)$ at the current sampling time $t_0$. Therefore, even if the measured point $D(t_0)$ deviates from the predicted point $W_s(t_0)$, it is still possible to correct the drawing position of the measured point $G(t_0)$ instantly, and display the respiratory waveform on the display unit 5 continuously.

With the biological information monitoring system 100 of this embodiment, in the subject number determination step S2, the number of subjects S on the bed BD is determined. Further, if there are a plurality of subjects S on the bed BD, then in the waveform separation step S6, it is possible to separate the respiratory oscillations of the plurality of subjects S and draw the respiratory waveform of each subject S. Therefore, for example, even if one patient is lying on the bed BD shared with a member of his/her family, it is still possible to reliably monitor the patient's respiratory waveform.

The biological information monitoring system 100 of this embodiment uses the load detectors 11 to 14 arranged under the legs of the bed BD to calculate the respiration rate of the subject S. Therefore, it is not necessary to attach any measuring device to the body of the subject S so that the subject S will not feel discomfort and sense of incongruity.

Modified Embodiments

It is possible to adopt the following modified embodiments in the biological information monitoring system 100 of the above embodiment.

For the above embodiment, the explanation was made with an example of performing the subject number determination step S2 before the oscillation coordinate setting step S3 and the waveform separation step S6. However, without being limited to that, the oscillation coordinate setting step S3 may be performed in parallel to the subject number determination step S2 and the waveform separation step S6. In a modified embodiment as follows, if the subject S is determined in the body motion determination step S1 showing no body motion, then the oscillation coordinate setting step S3 is started regardless of whether the number of subject S is one or not. Then, the subject number determination step S2 and the waveform separation step S6 are performed in parallel to the oscillation coordinate setting step S3. If there are a plurality of subjects S, then a center of gravity locus of each of the plurality of subjects S are separated in the waveform separation step S6 on the basis of the plurality of peak frequencies (that is, the plurality of subjects S) specified in the subject number determination step S2 and, on the basis of that, the oscillation coordinate setting step S3, the waveform drawing step S4 and the drawing compensation step S5 are performed.

In the tentative oscillation origin comparison steps S303, S306 and the like, the oscillation coordinate setting unit 34 of the biological information monitoring system 100 of the above embodiment determines whether or not the oscillation origin A can be set, based on a comparison between a predetermined value and the distance between the last tentative oscillation origin (lastly set tentative oscillation origin) and the tentative oscillation origin set right therebefore. However, the present disclosure is not limited to that.

As one example, the oscillation coordinate setting unit 34 may set the tentative oscillation origin and the tentative oscillation axis as many times as predetermined, and determine to let the last tentative oscillation origin and the last tentative oscillation axis be the oscillation origin O and the oscillation axis A. Further, the oscillation coordinate setting unit 34 may set each of the tentative oscillation origin and the tentative oscillation axis as many times as predetermined, and determine to let an average thereof be the oscillation origin O or the oscillation axis A.

From the oscillation coordinate setting unit 34, the waveform drawing unit 35 of the biological information monitoring system 100 of the above embodiment may receive information about the coordinate of the Nth extreme point EPN, the inclination of the Nth tentative coordinate axis TAN and the like, and appropriately adjust the scale of the graph area (drawing area) on the basis of the said information. For example, it is possible to adjust the scale of the vertical axis of the graph area (the distance $D_n$ axis; the displacement axis) on the basis of, for example, the distance between the first extreme point EP1 and the second extreme point EP2 along the direction of the second tentative oscillation axis TA2, and the maximum value (amplitude) of the distance D (displacement) calculated by using the determined oscillation origin O and oscillation axis A. By virtue of this, it is possible for the display unit 5 to constantly display the respiratory waveform at the most suitable scale for the observation.

In the above embodiment, the drawing compensation step S5 is performed for the respiratory waveform drawn through the oscillation coordinate setting step S3 and the waveform drawing step S4. However, without being limited to that, the drawing compensation step S5 may be applied to a respiratory waveform drawn by another method.

In the above embodiment, the drawing compensation unit 36 detects an occurrence of the small body motion or the large body motion on the basis of the distance between the predicted point $W_s(t_0)$ and the measured point $D(t_0)$. However, without being limited to that, for example, the oscillation coordinate setting unit 34 may determine that the small body motion or the large body motion has arisen and the stable respiration period has ended based on the fact that a distance between the position of the determined oscillation origin O and the position of the center of gravity G of the subject S exceeds a predetermined value, and the control unit 3 may return the process to the body motion determination step S1 in a case that the large body motion has arisen. It is possible to set the predetermined value on the basis of the distance between, for example, the first extreme point EP1 and the second extreme point EP2.

According to the above embodiment, in the predictive waveform generation step S501, the latest one period of the respiratory waveform $W_1$ is drawn (used) as the predictive waveform $W_s$. However, without being limited to that, the respiratory waveform of two previous periods or more may be modeled and the modeled waveform may be used as the predictive waveform $W_s$. Further, it is sufficient if the predictive waveform $W_s$ is distinguishable from the respiratory waveform $W_1$ being already drawn on the display unit 5, and thus, for example, the respiratory waveform $W_1$ and the predictive waveform $W_s$ may be drawn in different colors.

Figure 25:
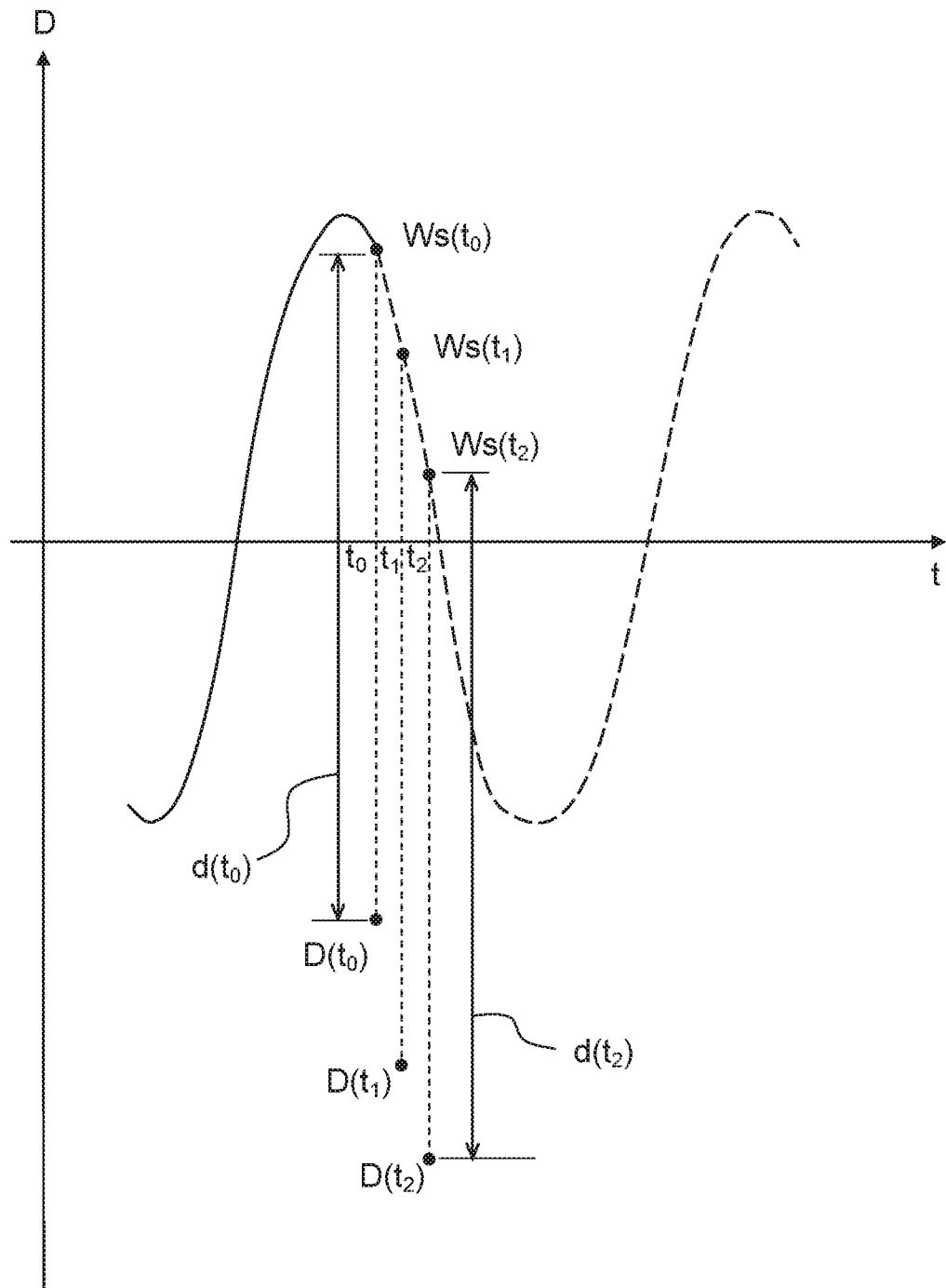
FIG. 25 is an illustrative view for explaining another method for drawing compensation.

In the correction distance calculation step S502 of the above embodiment, if the distance $d(t_0)$ at the sampling time $t_0$ is not less than the first threshold value $Th_1$ and not more than the second threshold value $Th_2$, then in the above embodiment, it is determined that the small body motion has arisen. However, for example, if the distances $d(t_1)$, $d(t_2)$ at the sampling times $t_1$, $t_2$ thereafter are far larger or far smaller than the distance $d(t_0)$, then regarding the period ranging from the sampling time $t_0$ to the sampling time $t_2$, it is proper to determine that the periodicity of the respiratory waveform before the sampling time $t_0$ is not maintained, and thus proper to stop the drawing of the respiratory waveform. Therefore, as depicted in FIG. 25, in each of a plurality of sampling times $t_0$ (in the example of FIG. 25, n=0, 1, 2), the distance $d(t_n)$ between the predicted point $W_s(t_n)$ and the measured point $D(t_n)$ is calculated and, if an average value of the distances $d(t_n)$ is not less than the first threshold value $Th_1$ and not more than the second threshold value $Th_2$, then the control unit 3 determines that the small body motion has arisen, and the average value of the distances $d(t_n)$ may be used as the correction distance. That is, each measured point $D(t_n)$ may be moved through the average value of the distances $d(t_n)$ in the direction of the oscillation axis A, for the drawing. According to this method, it is possible to raise the accuracy in determining the small body motion.

Alternatively, in each of the plurality of sampling times $t_n$ included in a predetermined time period (for example, ¼ of one period (cycle) of the predictive waveform $W_s$), the distance $d(t_n)$ between the predicted point $W_s(t_n)$ and the measured point $D(t_n)$ is calculated and, if the distance $d(t_n)$ has a constant value and is not less than the first threshold value $Th_1$ and not more than the second threshold value $Th_2$, then the control unit 3 determines that the small body motion has arisen, and the distances $d(t_n)$ may be used as the correction distance. That is, each measured point $D(t_n)$ may be moved through the distance $d(t_n)$ in the direction of the oscillation axis A, for the drawing. According to this method, it is possible to further raise the accuracy in determining the small body motion.

Further, after correcting the drawing position of the measured point $D(t_n)$ by any of the above methods, the correction distance calculation unit 362 may calculate the value Δx that make an integral value expressed by following numerical expression 3 minimum, and use the Δx as another correction distance.

$$\int_0^T \sqrt{W_s(t)-(D(t)-\Delta x))^2} dt \qquad \text{(Formula 3)}$$

Where T refers to the period of the predictive waveform $W_s$, $W_s(t)$ is an expression presenting the variation of predicted point as the function of the time t, and D(t) is an expression presenting the variation of measured point as the function of the time t. Then, Δx refers to another correction distance. By virtue of this, it is possible to more precisely compare the predictive waveform $W_s$ with the actual respiratory waveform after the drawing position is corrected.

Figure 26:
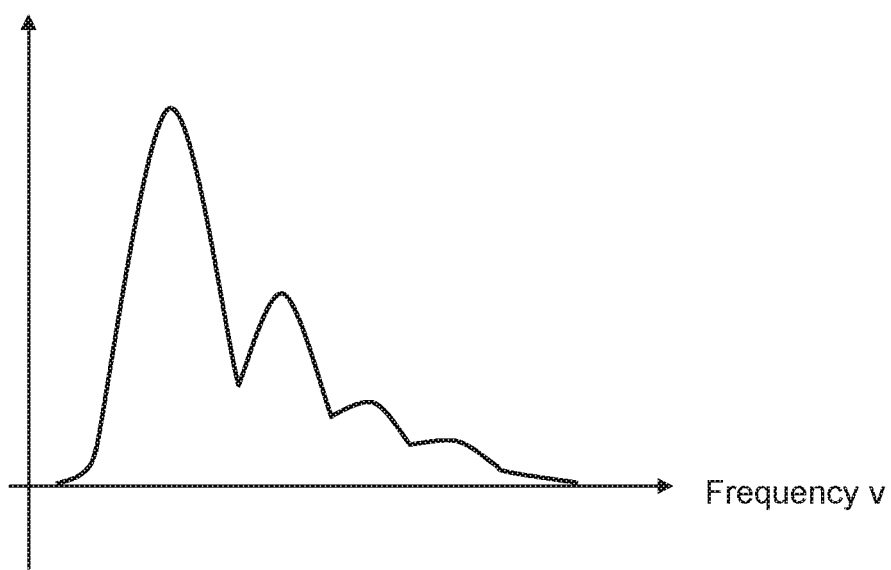
FIG. 26 shows an exemplary frequency profile of the subject.

In a case that the respiratory waveform of each subject S is drawn on the basis of the center of gravity locus corresponding to each of the frequencies calculated in the waveform separation step S6, each of the respiratory waveform is approximately sinusoidal because it is based on a calculation using a load component corresponding to one specific frequency. However, the actual respiratory waveform is constructed from a plurality of superimposed frequency components. Such frequency components include, for example, a frequency component caused by a difference between a velocity (pace) of inhalation and a velocity (pace) of exhalation, and/or a frequency component caused by difference in hold period in each of the inhalation and the exhalation. Therefore, if the respiratory pattern of each subject S is modeled beforehand, a respiratory waveform closer to the actual respiratory waveform may be drawn by selecting a plurality of peak frequencies from a frequency profile such as depicted in FIG. 26 and obtaining load components corresponding to the selected peaks.

Further, in the waveform separation step S6, the load component corresponding to the peak frequency specified in the subject number determination step S2 is calculated. However, the peak frequency specified in the subject number determination step S2 is biological information of the subject S, and is changeable. In view of that, the system may let the waveform of each of the subjects S to follow up the changing frequency of the subject S by specifying the frequency at regular interval and calculating a load component corresponding to the specified frequency. Specifically, by using a predetermined time length Δt capable of separating the already specified frequencies, and by dynamically changing the time of the Fourier integral, up to now, from the time as early as backward from now through the predetermined time length Δt, so as to calculate the coefficient peak seen between the current time and the time as early as backward from now through the predetermined time length Δt. By virtue of this, it is possible to catch the chronological change from the frequency already specified to the current frequency. Then, on the basis of the current frequency, by performing the steps from the waveform separation step S6, it is possible to cause the respiratory waveform of each subject S to follow up the changing frequency of that subject S.

In the subject number determination step S2 and the waveform separation step S6, the number of peak frequencies over the respiration range is determined to obtain the number of subjects S on the bed and the respiratory waveform of each subject S. However, by changing the range, it is possible to separate various pieces of biological information of each subject S. For example, by specifying the frequency peaks over the range from about 0.5 to about 3.3 Hz in the subject number determination step S2, it is also possible to separate and monitor the waveforms representing the heartbeats of a plurality of subjects S in the waveform separation step S6.

About the waveform separation step S6, the explanation was made on the premise of the plurality of subjects S being all human beings. However, without being limited to that, for example, even if there are one subject S and a device generating a periodical oscillation on the bed, it is still possible to separate the respiratory oscillation of the one subject S from the periodical oscillation due to the device.

The control unit 3 of the biological information monitoring system 100 of the above embodiment can also find the respiratory rate of the subject S by such a method as follows. Specifically for example, by causing the oscillation coordinate setting unit 34 to continue specifying the extreme points subsequently even after the oscillation origin O and the oscillation axis A are determined, the control unit 3 can obtain the respiratory rate of the subject S on the basis of the number of extreme points specified per unit time.

The biological information monitoring system 100 of the above embodiment may not have at least one of the oscillation coordinate setting unit 34, the drawing compensation unit 36, and the subject number determination unit in the control unit 3.

In the embodiment described above, each of the load detectors 11, 12, 13, 14 is not limited to the load sensor having the beam-type load cell. It is also possible to use, for example, a force sensor.

In the embodiment described above, the number of load detectors is not limited to four. It is also allowable to use five or more load detectors by providing an additional leg or additional legs for the bed BD. Alternatively, it is also allowable to arrange the load detectors for only three of the legs of the bed BD. Even when the three load detectors are used, it is possible to detect a position of the center of gravity G of the subject S on the plane of the bed BD provided that the three load detectors are not arranged on a straight line.

Figure 27:
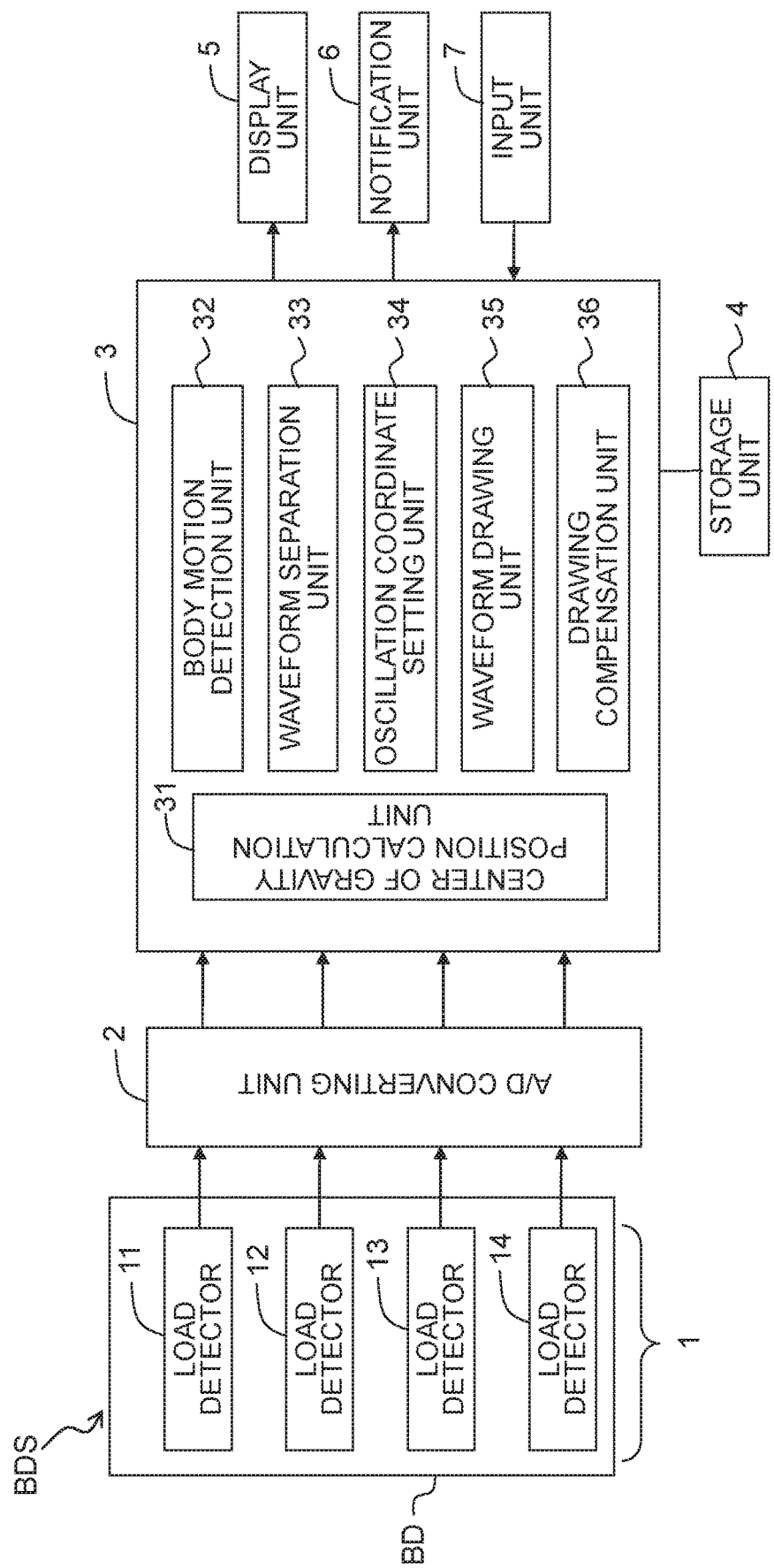
FIG. 27 is a block diagram depicting an overall configuration of a bed system according to a modified embodiment.

In the embodiment described above, the load detectors 11, 12, 13, 14 are arranged respectively on the undersides of the casters $C_1$, $C_2$, $C_3$, $C_4$ attached to the lower ends of the legs of the bed BD. However, there is no limitation thereto. Each of the load detectors 11, 12, 13, 14 may be provided respectively between one of the four legs of the bed BD and the board of the bed BD. Alternatively, if each of the four legs of the bed BD can be divided into upper and lower portions, each of the load detectors 11, 12, 13, 14 may be provided between upper leg and lower leg. Further alternatively, the load detectors 11, 12, 13, 14 may be formed integrally with the bed BD to construct a bed system BDS comprising the bed BD and the biological information monitoring system 100 of this embodiment (FIG. 27). Note that in this specification, the "load detectors placed in the bed" means the load detectors each of which is provided between one of the four legs of the bed BD and the board of the bed BD as described above and the load detectors each of which is provided between the upper leg and the lower leg.

In the embodiment described above, it is also allowable to provide a signal amplifying unit for amplifying the load signal fed from the load detecting unit 1 and/or a filtering unit for removing the noise from the load signal, between the load detecting unit 1 and the A/D converting unit 2.

In the biological information monitoring system 100 of the embodiment described above, the display unit 5 is not limited to the unit which displays the information on the monitor so that the user can make the visual recognition. For example, the display unit 5 may be a printer which periodically prints and outputs the respiratory condition (respiratory rate, respiratory ventilation volume), the state of the heartbeat, and the physical condition of the subject S. Alternatively, the display unit 5 may be a unit which performs the display by using any simple visual expression, for example, such that a blue lamp is turned ON if the subject S is under a sleeping state, a yellow lamp is turned ON if the subject S is under an awaken state, and/or a red lamp is turned ON if the subject S is under an apnea state. Further alternatively, the display unit 5 may be a unit which reports the respiratory condition and/or the physical condition of the subject S to the user by means of any sound or voice. Further alternatively, it is also allowable that the biological information monitoring system 100 does not have the display unit 5. The biological information monitoring system 100 may have only an output terminal for outputting the information. A monitor (display device) or the like, which is provided to perform the display, will be connected to the biological information monitoring system 100 by the aid of the output terminal.

The notification unit 6 of the embodiment described above performs the notification auditorily. However, the notification unit 6 may be constructed to perform the notification visually by means of, for example, the flashing or flickering of light. Alternatively, the notification unit 6 may be constructed to perform the notification by means of the vibration. Further, it is also allowable that the biological information monitoring system 100 of the embodiment described above does not have the notification unit 6.

The present invention is not limited to the embodiments described above provided that the feature of the present invention is maintained. Other embodiments, which are conceivable within the scope of the technical concept of the present invention, are also included in the scope of the present invention.

In the respiration waveform drawing system according to the above embodiments, the oscillation coordinate setting unit may be configured to perform: obtaining a third extreme point which appears at an opposite side of the tentative oscillation origin from the second extreme point, and at which a distance between the tentative oscillation origin and the position of the center of gravity of the subject shifting from the second extreme point is maximized; setting a direction connecting the second and third extreme points as a direction of an updated tentative oscillation axis; and setting a midpoint between the second and third extreme points as an updated tentative oscillation origin, and the waveform drawing unit may be configured to draw the respiratory waveform by presenting a displacement, from the updated tentative oscillation origin, of a position obtained by projecting the position of the center of gravity of the subject onto the updated tentative oscillation axis, with respect to time.

In the respiration waveform drawing system according to the above embodiments, the oscillation coordinate setting unit may be configured to perform comparing a separation distance between the initial origin and the tentative oscillation origin with a predetermined value, and to perform, in a case that the separation distance is more than the predetermined value, setting the updated tentative oscillation axis and the updated tentative oscillation origin.

In the respiration waveform drawing system according to the above embodiments, the oscillation coordinate setting unit may be configured to perform comparing a separation distance between the tentative oscillation origin and the updated tentative oscillation origin with a predetermined value, and to perform, in a case that the separation distance is more than the predetermined value: obtaining a fourth extreme point which appears at an opposite side of the updated tentative oscillation origin from the third extreme point, and at which a distance between the updated tentative oscillation origin and the position of the center of gravity of the subject shifting from the third extreme point is maximized; setting a direction connecting the third and fourth extreme points as a direction of a further updated tentative oscillation axis; and setting a midpoint between the third and fourth extreme points as a further updated tentative oscillation origin, and the waveform drawing unit may be configured to draw the respiratory waveform by presenting a displacement, from the further updated tentative oscillation origin, of a position obtained by projecting the position of the center of gravity of the subject onto the further updated tentative oscillation axis, with respect to time.

In the respiration waveform drawing system according to the above embodiments, the waveform drawing unit may be configured to draw the respiratory waveform by presenting a distance between the initial origin and the position of the center of gravity of the subject, with respect to time, until the center of gravity position of the subject reaches the first extreme point.

In the respiration waveform drawing system according to the above embodiments, the initial origin may be the position of the center of gravity of the subject at a time point at which a body motion of the subject ends.

The respiration waveform drawing system according to the above embodiments may further includes a drawing compensation unit configured to compensate a drawing state of the respiratory waveform, wherein the drawing compensation unit may include: a predictive waveform generation unit configured to generate a predictive waveform for the respiratory waveform of the subject based on the respiratory waveform in a past; and a correction distance calculation unit configured to calculate an inter-waveform distance between the respiratory waveform and the predictive waveform at a predetermined sampling time, the drawing compensation unit may be configured to compensate the drawing state of the respiratory waveform depending on the inter-waveform distance.

In the respiration waveform drawing system according to the above embodiments, the drawing compensation unit may be configured to perform determining whether the inter-waveform distance is within a predetermined range, and to perform, in a case that the inter-waveform distance is within the predetermined range, offsetting the respiratory waveform toward the predictive waveform by the inter-waveform distance.

According to the respiratory waveform drawing system of an aspect of the present disclosure, it is possible to present an almost real-time waveform indicating the respiration of the subject.

The invention claimed is:

1. A respiratory waveform drawing system for drawing a respiratory waveform of a subject on a bed, the system comprising:
    a plurality of load detectors which are to be placed in the bed or under legs of the bed, and which are configured to detect a load of the subject; and
    a controller configured to:
        obtain a position of a center of gravity of the subject based on the load of the subject;
        obtain a first extreme point at which a distance between an initial origin and the position of the center of gravity of the subject shifting from the initial origin is maximized, the position of the center of gravity of the subject at a certain time point being used as the initial origin;

obtain a second extreme point which appears at an opposite side of the initial origin from the first extreme point, and at which a distance between the initial origin and the position of the center of gravity of the subject shifting from the first extreme point is maximized;

set a direction connecting the first and second extreme points as a direction of a tentative oscillation axis;

set a midpoint between the first and second extreme points as a tentative oscillation origin; and draw, on a display, the respiratory waveform by presenting a displacement, from the tentative oscillation origin, of a position obtained by projecting the position of the center of gravity of the subject onto the tentative oscillation axis, with respect to time.

2. The respiratory waveform drawing system according to claim 1, wherein the controller is further configured to:

obtain a third extreme point which appears at an opposite side of the tentative oscillation origin from the second extreme point, and at which a distance between the tentative oscillation origin and the position of the center of gravity of the subject shifting from the second extreme point is maximized;

set a direction connecting the second and third extreme points as a direction of an updated tentative oscillation axis; and set a midpoint between the second and third extreme points as an updated tentative oscillation origin, and draw, on the display, the respiratory waveform by presenting a displacement, from the updated tentative oscillation origin, of a position obtained by projecting the position of the center of gravity of the subject onto the updated tentative oscillation axis, with respect to time.

3. The respiratory waveform drawing system according to claim 2, wherein the controller is further configured to compare a separation distance between the initial origin and the tentative oscillation origin with a predetermined value, and, in a case that the separation distance is more than the predetermined value, set the updated tentative oscillation axis and the updated tentative oscillation origin.

4. The respiratory waveform drawing system according to claim 2, wherein the controller is further configured to:

compare a separation distance between the tentative oscillation origin and the updated tentative oscillation origin with a predetermined value;

in a case that the separation distance is more than the predetermined value:

obtain a fourth extreme point which appears at an opposite side of the updated tentative oscillation origin from the third extreme point, and at which a distance between the updated tentative oscillation origin and the position of the center of gravity of the subject shifting from the third extreme point is maximized;

set a direction connecting the third and fourth extreme points as a direction of a further updated tentative oscillation axis; and set a midpoint between the third and fourth extreme points as a further updated tentative oscillation origin; and draw, on the display, the respiratory waveform by presenting a displacement, from the further updated tentative oscillation origin, of a position obtained by projecting the position of the center of gravity of the subject onto the further updated tentative oscillation axis, with respect to time.

5. The respiratory waveform drawing system according to claim 1, wherein the controller is further configured to draw, on the display, the respiratory waveform by presenting a distance between the initial origin and the position of the center of gravity of the subject, with respect to time, until the center of gravity position of the subject reaches the first extreme point.

6. The respiratory waveform drawing system according to claim 1, wherein the initial origin is the position of the center of gravity of the subject at a time point at which a body motion of the subject ends.

7. The respiratory waveform drawing system according to claim 1, wherein the controller is further configured to control the respiratory waveform drawing system to compensate the drawing of the respiratory waveform, wherein compensating the drawing of the respiratory waveform comprises:

generating a predictive waveform for the respiratory waveform of the subject based on the respiratory waveform in a past; and calculating an inter-waveform distance between the respiratory waveform and the predictive waveform at a predetermined sampling time, the controller being configured to compensate the drawing of the respiratory waveform depending on the inter-waveform distance.

8. The respiratory waveform drawing system according to claim 7, wherein the controller is further configured to determine whether the inter-waveform distance is within a predetermined range, and, in a case that the inter-waveform distance is within the predetermined range, offset the respiratory waveform toward the predictive waveform by the inter-waveform distance.

9. The respiratory waveform drawing system according to claim 1, wherein the controller is configured to draw the respiratory waveform in almost real-time.

* * * * *